(12) United States Patent
Kates

(10) Patent No.: US 7,528,711 B2
(45) Date of Patent: May 5, 2009

(54) PORTABLE MONITORING UNIT

(76) Inventor: Lawrence Kates, 1111 Bayside Dr., Corona Del Mar, CA (US) 92625

( * ) Notice: Subject to any disclaimer, the term of this patent is extended or adjusted under 35 U.S.C. 154(b) by 0 days.

(21) Appl. No.: 11/314,807

(22) Filed: Dec. 19, 2005

(65) Prior Publication Data

US 2007/0139183 A1 Jun. 21, 2007

(51) Int. Cl.
*G08B 29/00* (2006.01)

(52) U.S. Cl. .................. 340/506; 340/507; 340/3.1; 340/505; 340/10.1; 340/539.1; 340/825.36; 340/825.49

(58) Field of Classification Search ............. 340/506, 340/507, 3.1, 505, 539.1, 539.11, 10.1, 825.36, 340/825.49
See application file for complete search history.

(56) References Cited

U.S. PATENT DOCUMENTS

| | | | |
|---|---|---|---|
| 2,233,297 | A | 2/1941 | Polin et al. |
| 4,061,442 | A | 12/1977 | Clark et al. |
| 4,099,168 | A | 7/1978 | Kedjierski et al. |
| 4,136,823 | A | 1/1979 | Kulberg |
| 4,226,533 | A | 10/1980 | Snowman |
| 4,266,220 | A | 5/1981 | Malinowski |
| 4,400,694 | A | 8/1983 | Wong et al. |
| 4,420,746 | A | 12/1983 | Malinowski |
| 4,455,553 | A | 6/1984 | Johnson |
| 4,535,450 | A | 8/1985 | Tan |
| 4,543,570 | A | 9/1985 | Bressert et al. |
| 4,556,873 | A | 12/1985 | Yamada et al. |

(Continued)

FOREIGN PATENT DOCUMENTS

DE 3415786 A1 11/1984

(Continued)

OTHER PUBLICATIONS

Texas Instruments, Inc., Product catalog for "TRF6901 Single-Chip RF Transceiver," Copyright 2001-2003, 27 pages.

(Continued)

*Primary Examiner*—Daryl C Pope
(74) *Attorney, Agent, or Firm*—Knobbe, Martens, Olson & Bear, LLP

(57) ABSTRACT

A sensor system that provides an adjustable threshold level for the sensed quantity is described. The adjustable threshold allows the sensor to adjust to ambient conditions, aging of components, and other operational variations while still providing a relatively sensitive detection capability for hazardous conditions. The adjustable threshold sensor can operate for extended periods without maintenance or recalibration. A portable monitoring unit working in communication with the sensor system provides immediate communication of conditions detected by the sensors. The portable monitoring unit allows building or complex management to be in communication with a sensor system at all times without requiring someone to be physically present at a monitoring site. The portable monitoring unit can be equipped with an auditory device for alerting management or a screen for displaying pertinent information regarding an occurring situation so that management can quickly identify and resolve the problem. In addition, the portable monitoring unit can also be equipped with function keys that allow the portable monitoring unit to send instructions back to the sensor system. In one embodiment, the portable monitoring unit also includes a second transceiver for communications over a short wave radio frequency, or with a cellular phone system.

14 Claims, 15 Drawing Sheets

U.S. PATENT DOCUMENTS

| | | | |
|---|---|---|---|
| 4,652,859 A | 3/1987 | Van Wienen |
| 4,661,804 A | 4/1987 | Abel |
| 4,670,739 A | 6/1987 | Kelly, Jr. |
| 4,675,661 A | 6/1987 | Ishii |
| 4,692,742 A | 9/1987 | Raizen et al. |
| 4,692,750 A | 9/1987 | Murakami et al. |
| 4,727,359 A | 2/1988 | Yuchi et al. |
| 4,801,865 A | 1/1989 | Miller et al. |
| 4,811,011 A | 3/1989 | Sollinger |
| 4,817,131 A | 3/1989 | Thornborough et al. |
| 4,827,244 A | 5/1989 | Bellavia et al. |
| 4,862,514 A | 8/1989 | Kedjierski |
| 4,871,999 A | 10/1989 | Ishii et al. |
| 4,901,316 A | 2/1990 | Igarashi et al. |
| 4,916,432 A | 4/1990 | Tice et al. |
| 4,939,504 A | 7/1990 | Miller |
| 4,951,029 A | 8/1990 | Severson |
| 4,977,527 A | 12/1990 | Shaw et al. |
| 4,996,518 A | 2/1991 | Takahashi et al. |
| 5,107,446 A | 4/1992 | Shaw et al. |
| 5,134,644 A | 7/1992 | Garton et al. |
| 5,138,562 A | 8/1992 | Shaw et al. |
| 5,151,683 A | 9/1992 | Takahashi et al. |
| 5,159,315 A | 10/1992 | Schultz et al. |
| 5,168,262 A | 12/1992 | Okayama |
| 5,188,143 A | 2/1993 | Krebs |
| 5,229,750 A | 7/1993 | Welch, Jr. et al. |
| 5,240,022 A | 8/1993 | Franklin |
| 5,260,687 A | 11/1993 | Yamauchi et al. |
| 5,267,180 A | 11/1993 | Okayama |
| 5,281,951 A | 1/1994 | Okayama |
| 5,315,291 A | 5/1994 | Furr |
| 5,319,698 A | 6/1994 | Glidewell et al. |
| 5,335,186 A | 8/1994 | Tarrant |
| 5,345,224 A | 9/1994 | Brown |
| 5,357,241 A | 10/1994 | Welch et al. |
| 5,400,246 A * | 3/1995 | Wilson et al. ............ 700/17 |
| 5,408,223 A | 4/1995 | Guillemot |
| 5,430,433 A | 7/1995 | Shima |
| 5,432,500 A | 7/1995 | Scripps |
| 5,530,433 A | 6/1996 | Morita |
| 5,568,121 A | 10/1996 | Lamensdorf |
| 5,574,435 A | 11/1996 | Mochizuki |
| 5,627,515 A | 5/1997 | Anderson |
| 5,655,561 A | 8/1997 | Wendel et al. |
| 5,719,556 A | 2/1998 | Albin et al. |
| 5,736,928 A | 4/1998 | Tice et al. |
| 5,748,092 A | 5/1998 | Arsenault et al. |
| 5,854,994 A | 12/1998 | Canada et al. |
| 5,859,536 A | 1/1999 | Stockton |
| 5,881,951 A | 3/1999 | Carpenter |
| 5,889,468 A | 3/1999 | Banga |
| 5,892,758 A | 4/1999 | Argyroudis |
| 5,898,374 A | 4/1999 | Schepka |
| 5,907,491 A | 5/1999 | Canada et al. |
| 5,923,102 A | 7/1999 | Koenig et al. |
| 5,949,332 A | 9/1999 | Kim |
| 5,959,529 A * | 9/1999 | Kail, IV ............ 340/539.12 |
| 6,025,788 A | 2/2000 | Didick |
| 6,031,455 A * | 2/2000 | Grube et al. ........ 340/539.26 |
| 6,049,273 A | 4/2000 | Hess |
| 6,060,994 A | 5/2000 | Chen |
| 6,075,451 A | 6/2000 | Lebowitz et al. |
| 6,078,050 A | 6/2000 | Castleman |
| 6,078,269 A | 6/2000 | Markwell et al. |
| 6,084,522 A | 7/2000 | Addy |
| 6,097,288 A | 8/2000 | Koeppe, Jr. |
| 6,157,307 A | 12/2000 | Hardin |
| 6,175,310 B1 | 1/2001 | Gott |
| 6,208,247 B1 | 3/2001 | Agre et al. |
| 6,215,404 B1 | 4/2001 | Morales |
| 6,313,646 B1 | 11/2001 | Davis et al. |
| 6,320,501 B1 | 11/2001 | Tice et al. |
| 6,369,714 B2 | 4/2002 | Walter |
| 6,377,181 B1 | 4/2002 | Kroll et al. |
| 6,380,860 B1 | 4/2002 | Goetz |
| 6,420,973 B2 | 7/2002 | Acevedo |
| 6,437,692 B1 | 8/2002 | Petite et al. |
| 6,441,731 B1 | 8/2002 | Hess |
| 6,445,292 B1 | 9/2002 | Jen et al. |
| 6,489,895 B1 | 12/2002 | Apelman |
| 6,515,283 B1 | 2/2003 | Castleman et al. |
| 6,526,807 B1 | 3/2003 | Doumit et al. |
| 6,535,110 B1 | 3/2003 | Arora et al. |
| 6,552,647 B1 | 4/2003 | Thiessen et al. |
| 6,553,336 B1 | 4/2003 | Johnson et al. |
| 6,583,720 B1 | 6/2003 | Quigley |
| 6,639,517 B1 | 10/2003 | Chapman et al. |
| 6,666,086 B2 | 12/2003 | Colman et al. |
| 6,679,400 B1 | 1/2004 | Goodman |
| 6,704,681 B1 | 3/2004 | Nassof et al. |
| 6,731,215 B2 | 5/2004 | Harms et al. |
| 6,735,630 B1 | 5/2004 | Gelvin et al. |
| 6,748,804 B1 | 6/2004 | Lisec et al. |
| 6,759,956 B2 | 7/2004 | Menard et al. |
| 6,796,187 B2 | 9/2004 | Srinivasan et al. |
| 6,798,220 B1 | 9/2004 | Flanigan et al. |
| 6,826,948 B1 | 12/2004 | Bhatti et al. |
| 6,891,838 B1 | 5/2005 | Petite et al. |
| 6,892,751 B2 | 5/2005 | Sanders |
| 6,940,403 B2 | 9/2005 | Kail, IV |
| 6,995,676 B2 | 2/2006 | Amacher |
| 7,042,352 B2 | 5/2006 | Kates |
| 7,102,504 B2 | 9/2006 | Kates |
| 7,102,505 B2 | 9/2006 | Kates |
| 7,142,107 B2 | 11/2006 | Kates |
| 7,142,123 B1 | 11/2006 | Kates |
| 7,218,237 B2 | 5/2007 | Kates |
| 7,228,726 B2 | 6/2007 | Kates |
| 7,230,528 B2 | 6/2007 | Kates |
| 7,336,168 B2 | 2/2008 | Kates |
| 7,411,494 B2 | 8/2008 | Kates |
| 7,412,876 B2 | 8/2008 | Kates |
| 2002/0011570 A1 | 1/2002 | Castleman |
| 2002/0033759 A1 | 3/2002 | Morello |
| 2002/0084414 A1 | 7/2002 | Baker et al. |
| 2002/0186141 A1 | 12/2002 | Jen et al. |
| 2003/0011428 A1 | 1/2003 | Harms et al. |
| 2003/0058093 A1 | 3/2003 | Dohi et al. |
| 2003/0122677 A1 | 7/2003 | Kail, IV |
| 2003/0199247 A1 | 10/2003 | Striemer |
| 2004/0007264 A1 | 1/2004 | Bootka |
| 2005/0012601 A1 | 1/2005 | Matsubara et al. |
| 2005/0035877 A1 | 2/2005 | Kim |
| 2005/0105841 A1 | 5/2005 | Luo et al. |
| 2005/0116667 A1 | 6/2005 | Mueller et al. |
| 2005/0128067 A1 | 6/2005 | Zakrewski |
| 2005/0131652 A1 | 6/2005 | Corwin et al. |
| 2005/0258974 A1 | 11/2005 | Mahowald |
| 2005/0262923 A1 | 12/2005 | Kates |
| 2005/0275527 A1 | 12/2005 | Kates |
| 2005/0275528 A1 | 12/2005 | Kates |
| 2005/0275529 A1 | 12/2005 | Kates |
| 2005/0275530 A1 | 12/2005 | Kates |
| 2005/0275547 A1 | 12/2005 | Kates |
| 2006/0007008 A1 | 1/2006 | Kates |
| 2006/0032379 A1 | 2/2006 | Kates |
| 2006/0059977 A1 | 3/2006 | Kates |
| 2006/0267756 A1 | 11/2006 | Kates |
| 2006/0273896 A1 | 12/2006 | Kates |
| 2007/0063833 A1 | 3/2007 | Kates |
| 2007/0090946 A1 | 4/2007 | Kates |
| 2007/0211076 A1 | 9/2007 | Kates |
| 2007/0229237 A1 | 10/2007 | Kates |

| | | | |
|---|---|---|---|
| 2007/0234784 | A1 | 10/2007 | Kates |
| 2008/0141754 | A1 | 6/2008 | Kates |

FOREIGN PATENT DOCUMENTS

| | | |
|---|---|---|
| EP | 0070449 A1 | 7/1982 |
| EP | 0093463 A1 | 4/1983 |
| EP | 0 346 152 A2 | 12/1989 |
| EP | 0 346 152 A3 | 12/1989 |
| EP | 0441999 A1 | 8/1991 |
| EP | 0580298 A2 | 1/1997 |
| EP | 0930492 A1 | 7/1999 |
| EP | 0346152 A3 | 12/1999 |
| GB | 231458 | 1/1926 |
| GB | 2278471 A | 11/1994 |
| WO | WO 00-21047 A1 | 4/2000 |
| WO | WO 00-55825 A1 | 9/2000 |
| WO | WO 03-009631 A1 | 1/2003 |
| WO | WO 2004-010398 A1 | 1/2004 |
| WO | WO 2004-073326 A2 | 8/2004 |
| WO | WO 2004-100763 A2 | 11/2004 |
| WO | WO 2005-010837 A2 | 2/2005 |

OTHER PUBLICATIONS

Office Action dated Dec. 15, 2005 from Related U.S. Appl. No. 10/856,390.
Notice of Allowance dated Jun. 27, 2006 from Related U.S. Appl. No. 10/856,390.
Office Action dated Dec. 21, 2005 from Related U.S. Appl. No. 10/856,231.
Office Action dated Apr. 5, 2006 from Related U.S. Appl. No. 10/856,231.
Notice of Allowance dated Jun. 28, 2006 from Related U.S. Appl. No. 10/856,231.
Office Action dated Sep. 5, 2007 from Related U.S. Appl. No. 11/562,313.
Notice of Allowance dated Dec. 13, 2005 from Related U.S. Appl. No. 10/856,170.
Office Action dated Dec. 14, 2005 from Related U.S. Appl. No. 10/856,387.
Notice of Allowance dated Jun. 23, 2006 from Related U.S. Appl. No. 10/856,387.
Office Action dated Oct. 3, 2005 from Related U.S. Appl. No. 10/856,395.
Office Action dated Apr. 13, 2006 from Related U.S. Appl. No. 10/856,395.
Office Action dated Oct. 30, 2006 from Related U.S. Appl. No. 10/856,395.
Office Action dated Dec. 14, 2005 from Related U.S. Appl. No. 10/856,717.
Office Action dated May 31, 2006 from Related U.S. Appl. No. 10/856,717.
Notice of Allowance dated Mar. 13, 2007 from Related U.S. Appl. No. 10/856,717.
Office Action dated Dec. 30, 2005 from Related U.S. Appl. No. 10/948,628.
Office Action dated Apr. 20, 2006 from Related U.S. Appl. No. 10/948,628.
Office Action dated Sep. 9, 2006 from Related U.S. Appl. No. 10/948,628.
Notice of Allowance dated Apr. 9, 2007 from Related U.S. Appl. No. 10/948,628.
Supplemental Notice of Allowance dated May 3, 2007 from Related U.S. Appl. No. 10/948,628.
Office Action dated Apr. 27, 2006 from Related U.S. Appl. No. 11/145,880.
Office Action dated Mar. 1, 2007 from Related U.S. Appl. No. 11/145,880.
Notice of Allowance dated Jul. 5, 2007 from Related U.S. Appl. No. 11/145,880.
Supplemental Notice of Allowance dated Dec. 10, 2007 from Related U.S. Appl. No. 11/145,880.
Office Action dated Jul. 24, 2006 from Related U.S. Appl. No. 11/231,321.
Notice of Allowance dated Mar. 21, 2007 from Related U.S. Appl. No. 11/231,321.
Office Action dated Jul. 10, 2006 from Related U.S. Appl. No. 11/233,931.
Notice of Allowance dated Aug. 10, 2006 from Related U.S. Appl. No. 11/233,931.
Office Action dated Jan. 14, 2008 from Related U.S. Appl. No. 11/562,352.
Office Action dated Feb. 22, 2008 from Related U.S. Appl. No. 11/562,313.
Notice of Allowance dated May 23, 2008 from Related U.S. Appl. No. 11/562,313.
Office Action dated Mar. 4, 2008 from Related U.S. Appl. No. 11/216,225.
Office Action dated Jul. 10, 2008 from Related U.S. Appl. No. 11/216,225.
Office Action dated Jan. 16, 2008 from Related U.S. Appl. No. 11/761,760.
Office Action dated Jul. 1, 2008 from Related U.S. Appl. No. 11/761,760.
Office Action dated Aug. 21, 2008 from Related U.S. Appl. No. 11/562,352.

* cited by examiner

SENSOR MONITORING ALERT LEVELS

SEVERE
CALL FIRE DEPARTMENT,
SEND INFO & CONTACT OTHERS
ITEM FOR UPDATES — 1507

• • •

HIGH
SEND INFO TO MULTIPLE PMU's
AND OTHERS, WAIT FOR ACKNOWLEDGMENT
AND RESPONSE OR ELSE CALL FIRE DEPARTMENT — 1505

• • •

ELEVATED
SEND INFO, AND WAIT FOR
ACKNOWLEDGMENT AND/OR RESPONSE
OR ELSE CONTACT OTHERS — 1503

• • •

LOW
SEND INFO TO PMU — 1501

*FIG. 15*

PORTABLE MONITORING UNIT

BACKGROUND OF THE INVENTION

1. Field of the Invention

The present invention relates to a sensor in a wired or wireless sensor system for monitoring potentially dangerous or costly conditions such as, for example, smoke, temperature, water, gas and the like. It also relates to a portable monitoring unit for monitoring conditions present in a building, or complex.

2. Description of the Related Art

Maintaining and protecting a building or complex and its occupants is difficult and costly. Some conditions, such as fires, gas leaks, etc., are a danger to the occupants and the structure. Other malfunctions, such as water leaks in roofs, plumbing, etc., are not necessarily dangerous for the occupants, but can, nevertheless, cause considerable damage. In many cases, an adverse condition such as water leakage, fire, etc., is not detected in the early stages when the damage and/or danger is relatively small. This is particularly true of apartment complexes where there are many individual units and supervisory and/or maintenance personnel do not have unrestricted access to the apartments. When a fire or other dangerous condition develops, the occupant can be away from home, asleep, etc., and the fire alarm system can not signal an alarm in time to avoid major damage or loss of life.

Sensors can be used to detect such adverse conditions, but sensors present their own set of problems. For example, adding sensors, such as, for example, smoke detectors, water sensors, and the like in an existing structure can be prohibitively expensive due to the cost of installing wiring between the remote sensors and a centralized monitoring device used to monitor the sensors. Adding wiring to provide power to the sensors further increases the cost. Moreover, with regard to fire sensors, most fire departments will not allow automatic notification of the fire department based on the data from a smoke detector alone. Most fire departments require that a specific temperature rate-of-rise be detected before an automatic fire alarm system can notify the fire department. Unfortunately, detecting fire by temperature rate-of-rise generally means that the fire is not detected until it is too late to prevent major damage.

Compounding this problem, alarm systems do not provide actual measured data (e.g., measured smoke levels) to a remote monitoring panel. The typical fire alarm system is configured to detect a threshold level of smoke (or temperature) and trigger an alarm when the threshold is reached. Unfortunately, the threshold level must be placed relatively high to avoid false alarms and to allow for natural aging of components, and to allow for natural variations in the ambient environment. Setting the threshold to a relatively high level avoids false alarms, but reduces the effectiveness of the sensor and can unnecessarily put people and property at risk. Such a system is simple to operate but does not provide a sufficient "early warning" capability to allow supervisory personnel to respond to a fire in the very early stages. Moreover, even in a system with central or remote monitoring capability, someone must be present at all times at the monitoring site to see what is happening, increasing the cost of monitoring.

SUMMARY

These and other problems are solved by providing a sensor system that provides sensor information to a portable monitoring unit ("PMU") for alerting building or complex management, or other responsible parties, to a potential problem detected by the sensor system.

The PMU allows building or complex management to be in communication with the sensor system without requiring someone to be physically present at a monitoring site. In this respect, when a sensor communicates an alarm or other warning, the building or complex management will be quickly apprised of the situation. The early warning allows management to assess the situation and take early action, thereby reducing harm to the structure and any occupants present.

In one embodiment, the PMU operates in communication with the sensor monitoring system of a building, apartment, office, residence, etc. If the sensor system determines that the condition is an emergency (e.g., smoke has been detected), then the sensor system sends an alert message to the PMU. If the sensor system determines that the situation warrants reporting, but is not an emergency (e.g., low battery), then the sensor system can send a warning message to the PMU or can log the data for later reporting. Non-emergency information reported by the sensors can latter be sent to the PMU upon request, or upon the occurrence of a pre-defined event. In this way, building management can be informed of the conditions in and around the building without having to be present at a central location. In one embodiment, the sensor system detects and reports conditions such as, for example, smoke, temperature, humidity, moisture, water, water temperature, carbon monoxide, natural gas, propane gas, other flammable gases, radon, poison gasses, etc.

In one embodiment, the PMU can be small enough to be held in a hand, carried in a pocket, or clipped to a belt. In one embodiment, the PMU has a display screen for displaying communications. In one embodiment the PMU has one or more buttons or function keys for aiding in communication with the monitoring computer, repeaters or sensors. The function keys can be used to communicate one or more of the following: ACKNOWLEDGE receipt of message from monitoring computer; OK—situation has been taken care of or is a false alarm; PERFORM DIAGNOSTIC CHECK—check working status of sensors and repeaters; CALL FIRE DEPARTMENT; CALL TENANT; ALERT OTHERS; Turn ON/OFF POWER; TALK to others or tenant; SCROLL through screen display, adjust VOLUME, as well as any other communication or instruction which can be useful in a PMU.

The PMU can also include a transceiver in communication with a controller. The transceiver can be configured to send and receive communications between a monitoring computer and the controller. The controller can be configured to send an electrical signal to a screen display or to an audio device in order to alert management to a condition occurring. The controller can be configured to send and/or receive an electrical signal from a microphone, user input keys, a sensor programming interface, a location detector device, or a second transceiver for secondary communication channels (e.g., cellular phone or walkie talkie communication). The controller can also be connected to a computer interface, such as, for example, a USB port, in order to communicate via hard wire with a computer.

In one embodiment, the PMU can be configured to receive and send communication with a monitoring computer, repeaters, or sensors. For instance, the monitoring computer can send an Alert message indicating a serious condition is occurring. The PMU can display the message in the screen, or sound an alarm, or cause a pre-recorded message to play. The display can include any and all relevant information required to assess the situation such as the Alert type (e.g., FIRE), any relevant information about the Alert (e.g., rate of rise of smoke or temperature), the apartment or unit number, the specific room where the sensor is located, the phone number of the occupants, whether others have been notified or acknowledged the Alert, as well as any other information relevant in assessing the situation.

In one embodiment, the PMU can be configured to receive and communicate warning messages. For instance, the monitoring computer can send a message to the PMU warning that a battery is low in a particular sensor, that a sensor has been tampered with, that a heating unit or air conditioning unit needs maintenance, that a water leak has been detected, or any other relevant information that can be useful in maintaining a complex or building.

In one embodiment, the PMU can be configured to receive a diagnostic check of the sensors. The diagnostic check can check the battery level of the sensors and repeaters as well as checking the working status of each sensor or repeater or see which ones can need repair or replacement. The diagnostic check can also check the status of the heating, ventilation, and air conditioning systems. The diagnostic check can also be used to monitor any other conditions useful in maintaining a building or complex.

In one embodiment, depending on the severity of the alarm, when the monitoring computer communicates a message to the PMU such as an alert, the monitoring computer can wait for an acknowledgement communication to be sent from the PMU to the monitoring computer. If an acknowledgement is not received, the monitoring computer can attempt to contact other PMU's or can attempt to contact management through other communication channels, for instance, through a telephone communication, a cellular or other wireless communication, a pager, or through the internet. If the monitoring computer is still unable to contact management, the monitoring computer can alert the fire department directly that a situation is occurring at the building or complex. In one embodiment, the monitoring computer can also alert nearby units that a situation near them is occurring.

If an acknowledgment is received, depending on the severity of the alert, the monitoring computer can also wait for further instructions from the PMU. These instructions can include an OK communication alerting the monitoring computer that the situation has been taken care of or is simply a false alarm; an instruction to call the fire department; an instruction to call the tenants; an instruction to alert others; or any other useful instruction in dealing with the situation. If further instructions are not received, the monitoring computer can resend the alert, request further instructions from the PMU, attempt to contact other PMU's or can attempt to contact management through other channels, for instance, through a telephone communication, a cellular or other wireless communication, a pager, or through a network. If the monitoring computer is still unable to contact other management and fails to receive further instructions, the monitoring computer can alert the fire department directly that a situation is occurring at the building or complex.

In one embodiment, the severity or priority of the alarm can be based on the level of smoke, gas, water, temperature, etc. detected, the amount of time that the sensor has been alerting, the rate of rise of the substance detected, the number of sensors alerting to the situation, or any other sensor information useful in assessing the severity or priority level of the situation.

In one embodiment an adjustable threshold allows the sensor to adjust to ambient conditions, aging of components, and other operational variations while still providing a relatively sensitive detection capability for hazardous conditions. The adjustable threshold sensor can operate for an extended period of operability without maintenance or recalibration. In one embodiment, the sensor is self-calibrating and runs through a calibration sequence at startup or at periodic intervals. In one embodiment, the adjustable threshold sensor is used in an intelligent sensor system that includes one or more intelligent sensor units and a base unit that can communicate with the sensor units. When one or more of the sensor units detects an anomalous condition (e.g., smoke, fire, water, etc.) the sensor unit communicates with the base unit and provides data regarding the anomalous condition. The base unit can contact a supervisor or other responsible person by a plurality of techniques, such as, through a PMU, telephone, pager, cellular telephone, Internet (and/or local area network), etc. In one embodiment, one or more wireless repeaters are used between the sensor units and the base unit to extend the range of the system and to allow the base unit to communicate with a larger number of sensors.

In one embodiment, the adjustable-threshold sensor sets a threshold level according to an average value of the sensor reading. In one embodiment, the average value is a relatively long-term average. In one embodiment, the average is a time-weighted average wherein recent sensor readings used in the averaging process are weighted differently than less recent sensor readings. The average is used to set the threshold level. When the sensor reading rises above the threshold level, the sensor indicates an alarm condition. In one embodiment, the sensor indicates an alarm condition when the sensor reading rises above the threshold value for a specified period of time. In one embodiment, the sensor indicates an alarm condition when a statistical number of sensor readings (e.g., 3 of 2, 5 of 3, 10 of 7, etc.) are above the threshold level. In one embodiment, the sensor indicates various levels of alarm (e.g., notice, alert, alarm) based on how far above the threshold the sensor reading has risen and/or how rapidly the sensor reading has risen.

In one embodiment, the sensor system includes a number of sensor units located throughout a building that sense conditions and report anomalous results back to a central reporting station. The sensor units measure conditions that might indicate a fire, water leak, etc. The sensor units report the measured data to the base unit whenever the sensor unit determines that the measured data is sufficiently anomalous to be reported. The base unit can notify a responsible person such as, for example, a building manager, building owner, private security service, etc. In one embodiment, the sensor units do not send an alarm signal to the central location. Rather, the sensors send quantitative measured data (e.g., smoke density, temperature rate of rise, etc.) to the central reporting station.

In one embodiment, the sensor system includes a battery-operated sensor unit that detects a condition, such as, for example, smoke, temperature, humidity, moisture, water, water temperature, carbon monoxide, natural gas, propane gas, other flammable gases, radon, poison gasses, etc. The sensor unit is placed in a building, apartment, office, residence, etc. In order to conserve battery power, the sensor is normally placed in a low-power mode. In one embodiment, while in the low-power mode, the sensor unit takes regular sensor readings, adjusts the threshold level, and evaluates the readings to determine if an anomalous condition exists. If an anomalous condition is detected, then the sensor unit "wakes up" and begins communicating with the base unit or with a repeater. At programmed intervals, the sensor also "wakes up" and sends status information to the base unit (or repeater) and then listens for commands for a period of time.

In one embodiment, the sensor unit is bi-directional and configured to receive instructions from the central reporting station (or repeater). Thus, for example, the central reporting station can instruct the sensor to: perform additional measurements; go to a standby mode; wake up; report battery status; change wake-up interval; run self-diagnostics and report results; report its threshold level, change its threshold level, change its threshold calculation equation, change its alarm calculation equation, etc. In one embodiment, the sensor unit also includes a tamper switch. When tampering with the sensor is detected, the sensor reports such tampering to the base unit. In one embodiment, the sensor reports its general health and status to the central reporting station on a regular basis (e.g., results of self-diagnostics, battery health, etc.).

In one embodiment, the sensor unit provides two wake-up modes, a first wake-up mode for taking measurements (and reporting such measurements if deemed necessary), and a second wake-up mode for listening for commands from the central reporting station. The two wake-up modes, or combinations thereof, can occur at different intervals.

In one embodiment, the sensor units use spread-spectrum techniques to communicate with the base unit and/or the repeater units. In one embodiment, the sensor units use frequency-hopping spread-spectrum. In one embodiment, each sensor unit has an Identification code (ID) and the sensor units attaches its ID to outgoing communication packets. In one embodiment, when receiving wireless data, each sensor unit ignores data that is addressed to other sensor units.

The repeater unit is configured to relay communications traffic between a number of sensor units and the base unit. The repeater units typically operate in an environment with several other repeater units and thus, each repeater unit contains a database (e.g., a lookup table) of sensor IDs. During normal operation, the repeater only communicates with designated wireless sensor units whose IDs appear in the repeater's database. In one embodiment, the repeater is battery-operated and conserves power by maintaining an internal schedule of when it's designated sensors are expected to transmit and going to a low-power mode when none of its designated sensor units is scheduled to transmit. In one embodiment, the repeater uses spread-spectrum to communicate with the base unit and the sensor units. In one embodiment, the repeater uses frequency-hopping spread-spectrum to communicate with the base unit and the sensor units. In one embodiment, each repeater unit has an ID and the repeater unit attaches its ID to outgoing communication packets that originate in the repeater unit. In one embodiment, each repeater unit ignores data that is addressed to other repeater units or to sensor units not serviced by the repeater.

In one embodiment, the repeater is configured to provide bi-directional communication between one or more sensors and a base unit. In one embodiment, the repeater is configured to receive instructions from the central reporting station (or repeater). Thus, for example, the central reporting station can instruct the repeater to: send commands to one or more sensors; go to standby mode; "wake up"; report battery status; change wake-up interval; run self-diagnostics and report results; etc.

The base unit is configured to receive measured sensor data from a number of sensor units. In one embodiment, the sensor information is relayed through the repeater units. The base unit also sends commands to the repeater units and/or sensor units. In one embodiment, the base unit includes a diskless PC that runs off of a CD-ROM, flash memory, DVD, or other read-only device, etc. When the base unit receives data from a wireless sensor indicating that there can be an emergency condition (e.g., a fire or excess smoke, temperature, water, flammable gas, etc.) the base unit will attempt to notify a responsible party (e.g., a building manager) by several communication channels (e.g., telephone, Internet, pager, cell phone, etc.). In one embodiment, the base unit sends instructions to place the wireless sensor in an alert mode (inhibiting the wireless sensor's low-power mode). In one embodiment, the base unit sends instructions to activate one or more additional sensors near the first sensor.

In one embodiment, the base unit maintains a database of the health, battery status, signal strength, and current operating status of all of the sensor units and repeater units in the wireless sensor system. In one embodiment, the base unit automatically performs routine maintenance by sending commands to each sensor to run a self-diagnostic and report the results. The base unit collects such diagnostic results. In one embodiment, the base unit sends instructions to each sensor telling the sensor how long to wait between "wakeup" intervals. In one embodiment, the base unit schedules different wakeup intervals to different sensors based on the sensor's health, battery health, location, etc. In one embodiment, the base unit sends instructions to repeaters to route sensor information around a failed repeater.

BRIEF DESCRIPTION OF THE DRAWINGS

FIG. 15 is a graphical representation of a priority/response chart.

DETAILED DESCRIPTION OF THE PREFERRED EMBODIMENT

Figure 1:
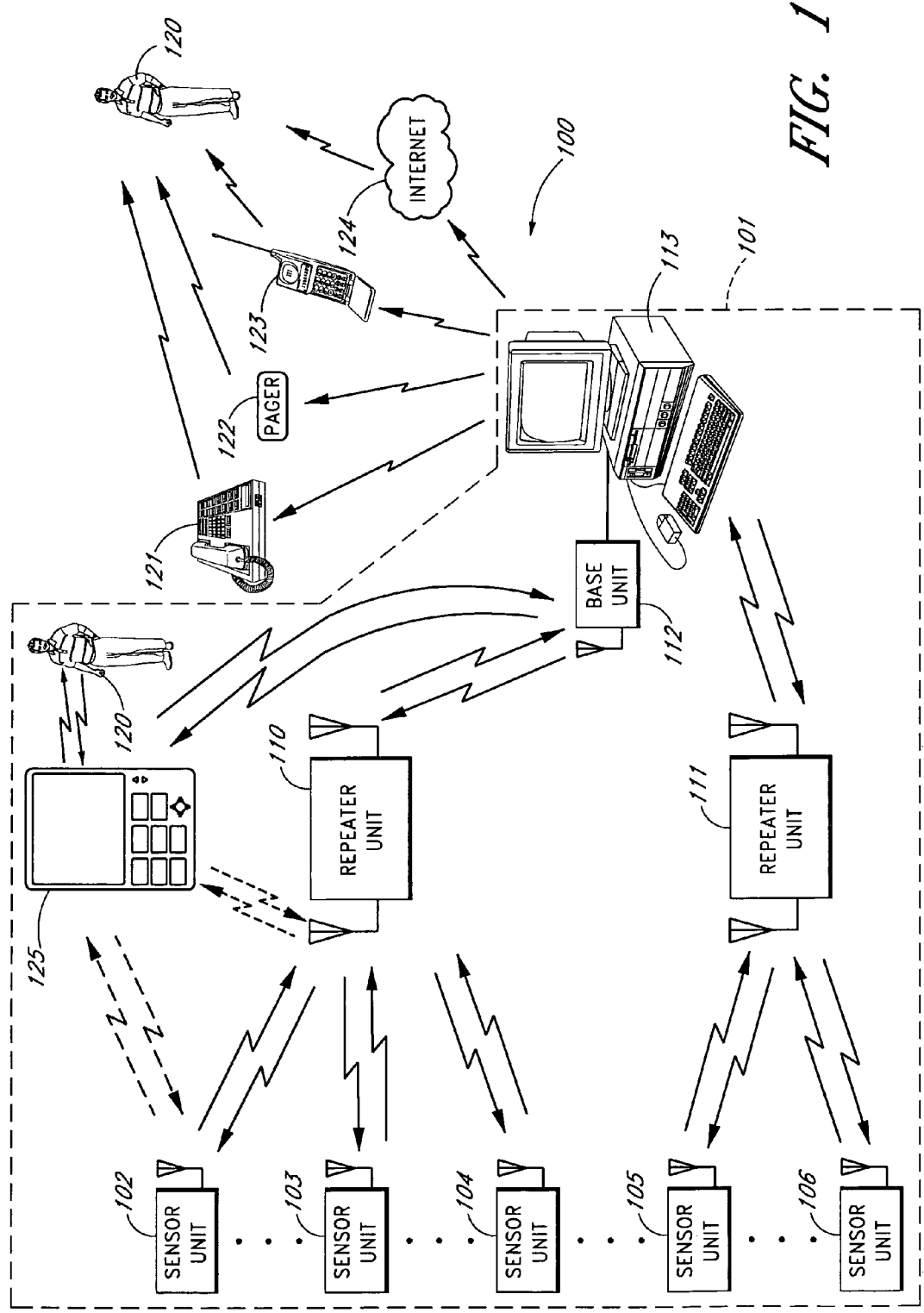
FIG. 1 shows sensor system that includes a plurality of sensor units that communicate with a base unit through a number of repeater units and also communicates with a PMU.

FIG. 1 shows a sensor system 100 that includes a plurality of sensor units 102-106 that communicate with a base unit 112 through a number of repeater units 110-111. The sensor units 102-106 are located throughout a building 101. Sensor units 102-104 communicate with the repeater 110. Sensor units 105-106 communicate with the repeater 111. The repeaters 110-111 communicate with the base unit 112. The base unit 112 communicates with a monitoring computer system 113 through a computer network connection such as, for example, Ethernet, wireless Ethernet, firewire port, Universal Serial Bus (USB) port, Bluetooth, etc. The computer system 113 contacts a building manager, maintenance service, alarm service, or other responsible personnel 120 using one or more of several communication systems such as, for example, PMU 125, telephone 121, pager 122, cellular telephone 123 (e.g., direct contact, voicemail, text, etc.), and/or through the Internet and/or local area network 124 (e.g., through email, instant messaging, network communications, etc.). In one embodiment, multiple base units 112 are provided to the monitoring computer 113. In one embodiment, the monitoring computer 113 is provided to more than one computer monitors, thus, allowing more data to be displayed than can conveniently be displayed on a single monitor. In one embodiment, the monitoring computer 113 is provided to multiple monitors located in different locations, thus allowing the data from the monitoring computer 113 to be displayed in multiple locations.

The sensor units 102-106 include sensors to measure conditions, such as, for example, smoke, temperature, moisture, water, water temperature, humidity, carbon monoxide, natural gas, propane gas, security alarms, intrusion alarms (e.g., open doors, broken windows, open windows, and the like), other flammable gases, radon, poison gasses, etc. Different sensor units can be configured with different sensors or with combinations of sensors. Thus, for example, in one installation the sensor units 102 and 104 could be configured with smoke and/or temperature sensors while the sensor unit 103 could be configured with a humidity sensor.

The discussion that follows generally refers to the sensor unit 102 as an example of a sensor unit, with the understanding that the description of the sensor unit 102 can be applied to many sensor units. Similarly, the discussion generally refers to the repeater 110 by way of example, and not limitation. It will also be understood by one of ordinary skill in the art that repeaters are useful for extending the range of the sensor units 102-106 but are not required in all embodiments. Thus, for example, in one embodiment, one or more of the sensor units 102-106 can communicate directly with the base unit 112 without going through a repeater. It will also be understood by one of ordinary skill in the art that FIG. 1 shows only five sensor units (102-106) and two repeater units (110-111) for purposes of illustration and not by way of limitation. An installation in a large apartment building or complex would typically involve many sensor units and repeater units. Moreover, one of ordinary skill in the art will recognize that one repeater unit can service relatively many sensor units. In one embodiment, the sensor units 102 can communicate directly with the base unit 112 without going through a repeater 111.

When the sensor unit 102 detects an anomalous condition (e.g., smoke, fire, water, etc.) the sensor unit communicates with the appropriate repeater unit 110 and provides data regarding the anomalous condition. The repeater unit 110 forwards the data to the base unit 112, and the base unit 112 forwards the information to the computer 113. The computer 113 evaluates the data and takes appropriate action. If the computer 113 determines that the condition is an emergency (e.g., fire, smoke, large quantities of water), then the computer 113 contacts the appropriate personnel 120. If the computer 113 determines that a the situation warrants reporting, but is not an emergency, then the computer 113 can log the data for later reporting, or can send a warning message to the PMU 125. In this way, the sensor system 100 can monitor the conditions in and around the building 101.

In one embodiment, the sensor unit 102 has an internal power source (e.g., battery, solar cell, fuel cell, etc.). In order to conserve power, the sensor unit 102 is normally placed in a low-power mode. In one embodiment, using sensors that require relatively little power, while in the low-power mode the sensor unit 102 takes regular sensor readings and evaluates the readings to determine if an anomalous condition exists. In one embodiment, using sensors that require relatively more power, while in the low-power mode, the sensor unit 102 takes and evaluates sensor readings at periodic intervals. If an anomalous condition is detected, then the sensor unit 102 "wakes up" and begins communicating with the base unit 112 through the repeater 110. At programmed intervals, the sensor unit 102 also "wakes up" and sends status information (e.g., power levels, self diagnostic information, etc.) to the base unit (or repeater) and then listens for commands for a period of time. In one embodiment, the sensor unit 102 also includes a tamper detector. When tampering with the sensor unit 102 is detected, the sensor unit 102 reports such tampering to the base unit 112.

In one embodiment, the sensor unit 102 provides bi-directional communication and is configured to receive data and/or instructions from the base unit 112. Thus, for example, the base unit 112 can instruct the sensor unit 102 to perform additional measurements, to go to a standby mode, to wake up, to report battery status, to change wake-up interval, to run self-diagnostics and report results, etc. In one embodiment, the sensor unit 102 reports its general health and status on a regular basis (e.g., results of self-diagnostics, battery health, etc.)

In one embodiment, the sensor unit 102 provides two wake-up modes, a first wake-up mode for taking measurements (and reporting such measurements if deemed necessary), and a second wake-up mode for listening for commands from the central reporting station. The two wake-up modes, or combinations thereof, can occur at different intervals.

In one embodiment, the sensor unit 102 use spread-spectrum techniques to communicate with the repeater unit 110. In one embodiment, the sensor unit 102 use frequency-hopping spread-spectrum. In one embodiment, the sensor unit 102 has an address or identification (ID) code that distinguishes the sensor unit 102 from the other sensor units. The sensor unit 102 attaches its ID to outgoing communication packets so that transmissions from the sensor unit 102 can be identified by the repeater 110. The repeater 110 attaches the ID of the sensor unit 102 to data and/or instructions that are transmitted to the sensor unit 102. In one embodiment, the sensor unit 102 ignores data and/or instructions that are addressed to other sensor units.

In one embodiment, the sensor unit 102 includes a reset function. In one embodiment, the reset function is activated by the reset switch 208. In one embodiment, the reset function is active for a prescribed interval of time. During the reset interval, the transceiver 203 is in a receiving mode and can receive the identification code from an external programmer. In one embodiment, the external programmer wirelessly transmits a desired identification code. In one embodiment, the identification code is programmed by an external programmer that is connected to the sensor unit 102 through an electrical connector. In one embodiment, the electrical connection to the sensor unit 102 is provided by sending modulated control signals (power line carrier signals) through a connector used to connect the power source 206. In one embodiment, the external programmer provides power and control signals. In one embodiment, the external programmer also programs the type of sensor(s) installed in the sensor unit. In one embodiment, the identification code includes an area code (e.g., apartment number, zone number, floor number, etc.) and a unit number (e.g., unit 1, 2, 3, etc.). In one embodiment, the PMU is used to program the sensor unit 102.

In one embodiment, the sensor communicates with the repeater on the 900 MHz band. This band provides good transmission through walls and other obstacles normally found in and around a building structure. In one embodiment, the sensor communicates with the repeater on bands above and/or below the 900 MHz band. In one embodiment, the sensor, repeater, and/or base unit listens to a radio frequency channel before transmitting on that channel or before beginning transmission. If the channel is in use, (e.g., by another device such as another repeater, a cordless telephone, etc.) then the sensor, repeater, and/or base unit changes to a different channel. In one embodiment, the sensor, repeater, and/or base unit coordinate frequency hopping by listening to radio frequency channels for interference and using an algorithm to select a next channel for transmission that avoids the interference. Thus, for example, in one embodiment, if a sensor senses a dangerous condition and goes into a continuous transmission mode, the sensor will test (e.g., listen to) the channel before transmission to avoid channels that are blocked, in use, or jammed. In one embodiment, the sensor continues to transmit data until it receives an acknowledgement from the base unit that the message has been received. In one embodiment, the sensor transmits data having a normal priority (e.g., status information) and does not look for an acknowledgement, and the sensor transmits data having elevated priority (e.g., excess smoke, temperature, etc.) until an acknowledgement is received.

The repeater unit 10 is configured to relay communications traffic between the sensor 102 (and similarly, the sensor units 103-104) and the base unit 112. The repeater unit 110 typically operates in an environment with several other repeater units (such as the repeater unit 111 in FIG. 1) and thus, the repeater unit 110 contains a database (e.g., a lookup table) of sensor unit IDs. In FIG. 1, the repeater 110 has database entries for the Ids of the sensors 102-104, and thus, the sensor 110 will only communicate with sensor units 102-104. In one embodiment, the repeater 110 has an internal power source (e.g., battery, solar cell, fuel cell, etc.) and conserves power by maintaining an internal schedule of when the sensor units 102-104 are expected to transmit. In one embodiment, the repeater unit 110 goes to a low-power mode when none of its designated sensor units is scheduled to transmit. In one embodiment, the repeater 110 uses spread-spectrum techniques to communicate with the base unit 112 and with the sensor units 102-104. In one embodiment, the repeater 110 uses frequency-hopping spread-spectrum to communicate with the base unit 112 and the sensor units 102-104. In one embodiment, the repeater unit 110 has an address or identification (ID) code and the repeater unit 110 attaches its address to outgoing communication packets that originate in the repeater (that is, packets that are not being forwarded). In one embodiment, the repeater unit 110 ignores data and/or instructions that are addressed to other repeater units or to sensor units not serviced by the repeater 110.

In one embodiment, the base unit 112 communicates with the sensor unit 102 by transmitting a communication packet addressed to the sensor unit 102. The repeaters 110 and 111 both receive the communication packet addressed to the sensor unit 102. The repeater unit 111 ignores the communication packet addressed to the sensor unit 102. The repeater unit 110 transmits the communication packet addressed to the sensor unit 102 to the sensor unit 102. In one embodiment, the sensor unit 102, the repeater unit 110, and the base unit 112 communicate using Frequency-Hopping Spread Spectrum (FHSS), also known as channel-hopping.

Frequency-hopping wireless systems offer the advantage of avoiding other interfering signals and avoiding collisions. Moreover, there are regulatory advantages given to systems that do not transmit continuously at one frequency. Channel-hopping transmitters change frequencies after a period of continuous transmission, or when interference is encountered. These systems can have higher transmit power and relaxed limitations on in-band spurs. FCC regulations limit transmission time on one channel to 400 milliseconds (averaged over 10-20 seconds depending on channel bandwidth) before the transmitter must change frequency. There is a minimum frequency step when changing channels to resume transmission. If there are 25 to 49 frequency channels, regulations allow effective radiated power of 24 dBm, spurs must be −20 dBc, and harmonics must be −41.2 dBc. With 50 or more channels, regulations allow effective radiated power to be up to 30 dBm.

In one embodiment, the sensor unit 102, the repeater unit 110, and the base unit 112 communicate using FHSS wherein the frequency hopping of the sensor unit 102, the repeater unit 110, and the base unit 112 are not synchronized such that at any given moment, the sensor unit 102 and the repeater unit 110 are on different channels. In such a system, the base unit 112 communicates with the sensor unit 102 using the hop frequencies synchronized to the repeater unit 110 rather than the sensor unit 102. The repeater unit 110 then forwards the data to the sensor unit using hop frequencies synchronized to the sensor unit 102. Such a system largely avoids collisions between the transmissions by the base unit 112, the PMU 125, and the repeater unit 110.

In one embodiment, the sensor units 102-106 all use FHSS and the sensor units 102-106 are not synchronized. Thus, at any given moment, it is unlikely that any two or more of the sensor units 102-106 will transmit on the same frequency. In this manner, collisions are largely avoided. In one embodiment, collisions are not detected but are tolerated by the system 100. If a collisions does occur, data lost due to the collision is effectively re-transmitted the next time the sensor units transmit sensor data. When the sensor units 102-106 and repeater units 110-111 operate in asynchronous mode, then a second collision is highly unlikely because the units causing the collisions have hopped to different channels. In one embodiment, the sensor units 102-106, repeater units 110-111, PMU 125, and the base unit 112 use the same hop rate. In one embodiment, the sensor units 102-106, repeater units 110-111, PMU 125, and the base unit 112 use the same pseudo-random algorithm to control channel hopping, but with different starting seeds. In one embodiment, the starting seed for the hop algorithm is calculated from the ID of the sensor units 102-106, repeater units 110-111, PMU 125, or the base unit 112.

In an alternative embodiment, the base unit communicates with the sensor unit 102 by sending a communication packet addressed to the repeater unit 110, where the packet sent to the repeater unit 110 includes the address of the sensor unit 102. The repeater unit 102 extracts the address of the sensor unit 102 from the packet and creates and transmits a packet addressed to the sensor unit 102.

In one embodiment, the repeater unit 110 is configured to provide bi-directional communication between its sensors and the base unit 112. In one embodiment, the repeater 110 is configured to receive instructions from the base unit 112. Thus, for example, the base unit 112 can instruct the repeater to: send commands to one or more sensors; go to standby mode; "wake up"; report battery status; change wake-up interval; run self-diagnostics and report results; etc.

The base unit 112 is configured to receive measured sensor data from a number of sensor units either directly, or through the repeaters 110-111. The base unit 112 also sends commands to the repeater units 110-111 and/or to the sensor units 102-106. In one embodiment, the base unit 112 communicates with a diskless computer 113 that runs off of a CD-ROM. When the base unit 112 receives data from a sensor unit 102-106 indicating that there can be an emergency condition (e.g., a fire or excess smoke, temperature, water, etc.) the computer 113 will attempt to notify the responsible party 120.

In one embodiment, the computer 112 maintains a database of the health, power status (e.g., battery charge), and current operating status of all of the sensor units 102-106 and the repeater units 110-111. In one embodiment, the computer 113 automatically performs routine maintenance by sending commands to each sensor unit 102-106 to run a self-diagnostic and report the results. The computer 113 collects and logs such diagnostic results. In one embodiment, the computer 113 sends instructions to each sensor unit 102-106 telling the sensor how long to wait between "wakeup" intervals. In one embodiment, the computer 113 schedules different wakeup intervals to different sensor unit 102-106 based on the sensor unit's health, power status, location, etc. In one embodiment, the computer 113 schedules different wakeup intervals to different sensor unit 102-106 based on the type of data and urgency of the data collected by the sensor unit (e.g., sensor units that have smoke and/or temperature sensors produce data that should be checked relatively more often than sensor units that have humidity or moisture sensors). In one embodiment, the base unit sends instructions to repeaters to route sensor information around a failed repeater.

In one embodiment, the computer 113 produces a display that tells maintenance personnel which sensor units 102-106 need repair or maintenance. In one embodiment, the computer 113 maintains a list showing the status and/or location of each sensor according to the ID of each sensor.

In one embodiment, the sensor units 102-106 and /or the repeater units 110-111 measure the signal strength of the wireless signals received (e.g., the sensor unit 102 measures the signal strength of the signals received from the repeater unit 110, the repeater unit 110 measures the signal strength received from the sensor unit 102 and/or the base unit 112). The sensor units 102-106 and /or the repeater units 110-111 report such signal strength measurement back to the computer 113. The computer 113 evaluates the signal strength measurements to ascertain the health and robustness of the sensor system 100. In one embodiment, the computer 113 uses the signal strength information to re-route wireless communications traffic in the sensor system 100. Thus, for example, if the repeater unit 110 goes offline or is having difficulty communicating with the sensor unit 102, the computer 113 can send instructions to the repeater unit 111 to add the ID of the sensor unit 102 to the database of the repeater unit 111 (and similarly, send instructions to the repeater unit 110 to remove the ID of the sensor unit 102), thereby routing the traffic for the sensor unit 102 through the router unit 111 instead of the router unit 110.

In one embodiment, a PMU 125 communicates with the sensor system 100. It will be understood by a person of skill in the art that the PMU 125 can communicate with various sensor systems. The description that follows of the PMU 125 is meant by way of explanation and not by way of limitation. In one embodiment, the monitoring computer 113 sends any required communications to the PMU 125 which conveys the information to management 120. The monitoring computer 113 can send the communication through base unit 112, or through any other communication channels. Optionally, the sensor units and repeater units can communicate directly with the PMU 1.

In one embodiment, one or more PMUs can communicate with the monitoring computer 113 at the same time. PMU 125 can be configured individually so that only certain PMUs can communicate with the system, or PMU 125 can be configured to communicate with multiple systems. PMU 125 can also be configured to identify the user. Different authorization levels can be given to different users to allow different access levels to the sensor system.

In one embodiment, the PMU 125 uses spread-spectrum techniques to communicate with the sensor units, repeater units, or base unit 112. In one embodiment, the PMU 125 uses frequency-hopping spread-spectrum. In one embodiment, the PMU 125 has an address or identification (ID) code that distinguishes the PMU 125 from the other PMUs. The PMU 125 can attach its ID to outgoing communication packets so that transmissions from the PMU 125 can be identified by the base 112, sensor units, or repeater units.

In one embodiment, the sensor units, the repeater units, the base unit, and the PMU 125 communicate using FHSS wherein the frequency hopping of the sensor units, the repeater units, the base unit, and the PMU 125 are not synchronized such that at any given moment, the sensor units and the repeater units are on different channels. In such a system, the base unit 112 or PMU 125 communicates with the sensor units using the hop frequencies synchronized to the repeater units rather than the sensor units. The repeater units then forward the data to the sensor units using hop frequencies synchronized to the sensor units. Such a system largely avoids collisions between the transmissions by the base unit 112, the PMU 125, and the repeater units.

In one embodiment, the sensor units communicate with the repeater units, base 112, or PMU 125 on the 900 MHz band. This band provides good transmission through walls and other obstacles normally found in and around a building structure. In one embodiment, the sensor units communicate with the repeater units, base 112, or PMU 125 on bands above and/or below the 900 MHz band. In one embodiment, the sensor units, repeater units, base unit 112, and/or PMU 125 listen to a radio frequency channel before transmitting on that channel or before beginning transmission. If the channel is in use, (e.g., by another device such as another repeater unit, a cordless telephone, etc.) then the sensor units, repeater units, base unit 112, and/or PMU 125 change to a different channel. In one embodiment, the sensor units, repeater units, base unit 112 and/or PMU 125 coordinate frequency hopping by listening to radio frequency channels for interference and using an algorithm to select a next channel for transmission that avoids the interference. Thus, for example, in one embodiment, if a PMU 125 is instructed to send a communication, the PMU 125 will test (e.g., listen to) the channel before transmission to avoid channels that are blocked, in use, or jammed.

Figure 2:
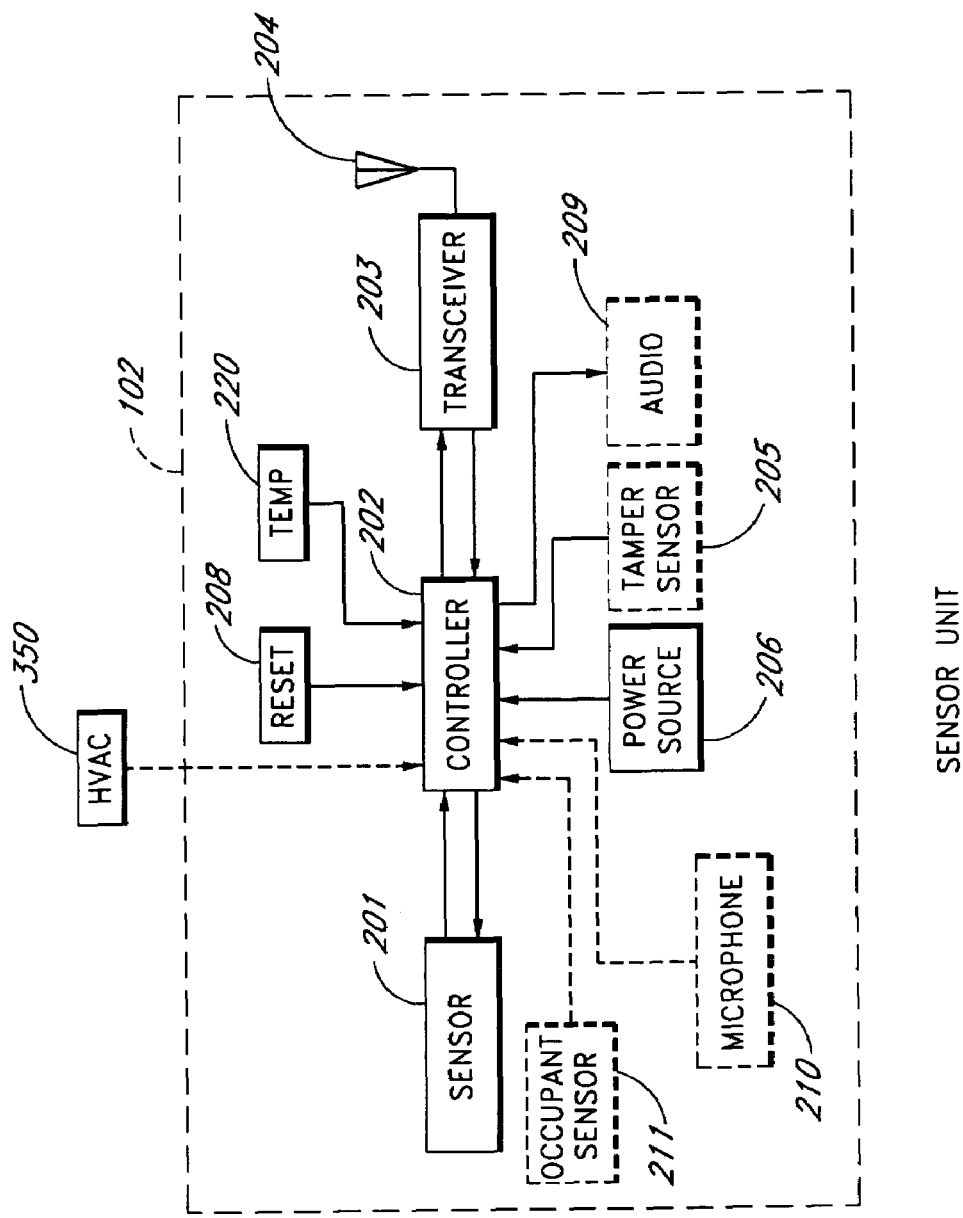
FIG. 2 is a block diagram of a sensor unit.

FIG. 2 is a block diagram of the sensor unit 102. In the sensor unit 102, one or more sensors 201 and a transceiver 203 are provided to a controller 202. The controller 202 typically provides power, data, and control information to the sensor(s) 201 and the transceiver 202. A power source 206 is provided to the controller 202. An optional tamper sensor 205 is also provided to the controller 202. A reset device (e.g., a switch) 208 is proved to the controller 202. In one embodiment, an optional audio output device 209 is provided. In one embodiment, the sensor 201 is configured as a plug-in module that can be replaced relatively easily. In one embodiment, a temperature sensor 220 is provided to the controller 202. In one embodiment, the temperature sensor 220 is configured to measure ambient temperature.

In one embodiment, the transceiver 203 is based on a TRF 6901 transceiver chip from Texas Instruments, Inc. In one embodiment, the controller 202 is a conventional programmable microcontroller. In one embodiment, the controller 202 is based on a Field Programmable Gate Array (FPGA), such as, for example, provided by Xilinx Corp. In one embodiment, the sensor 201 includes an optoelectric smoke sensor with a smoke chamber. In one embodiment, the sensor 201 includes a thermistor. In one embodiment, the sensor 201 includes a humidity sensor. In one embodiment, the sensor 201 includes a sensor, such as, for example, a water level sensor, a water temperature sensor, a carbon monoxide sensor, a moisture sensor, a water flow sensor, natural gas sensor, propane sensor, etc.

The controller 202 receives sensor data from the sensor(s) 201. Some sensors 201 produce digital data. However, for many types of sensors 201, the sensor data is analog data. Analog sensor data is converted to digital format by the controller 202. In one embodiment, the controller evaluates the data received from the sensor(s) 201 and determines whether the data is to be transmitted to the base unit 112. The sensor unit 102 generally conserves power by not transmitting data that falls within a normal range. In one embodiment, the controller 202 evaluates the sensor data by comparing the data value to a threshold value (e.g., a high threshold, a low threshold, or a high-low threshold). If the data is outside the threshold (e.g., above a high threshold, below a low threshold, outside an inner range threshold, or inside an outer range threshold), then the data is deemed to be anomalous and is transmitted to the base unit 112. In one embodiment, the data threshold is programmed into the controller 202. In one embodiment, the data threshold is programmed by the base unit 112 by sending instructions to the controller 202. In one embodiment, the controller 202 obtains sensor data and transmits the data when commanded by the computer 113.

In one embodiment, the tamper sensor 205 is configured as a switch that detects removal of/or tampering with the sensor unit 102.

Figure 3:
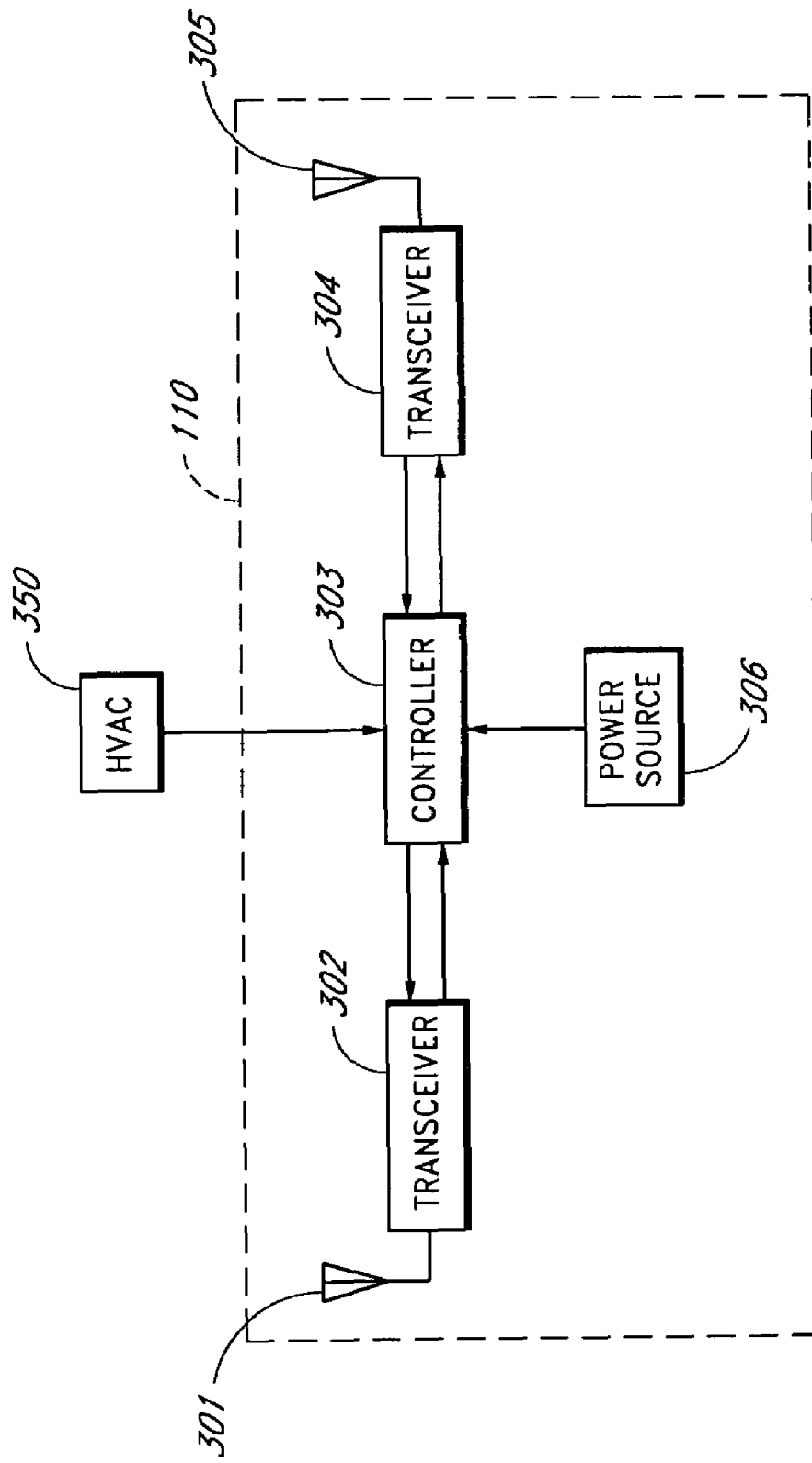
FIG. 3 is a block diagram of a repeater unit.

FIG. 3 is a block diagram of the repeater unit 110. In the repeater unit 110, a first transceiver 302 and a second transceiver 304 are provided to a controller 303. The controller 303 typically provides power, data, and control information to the transceivers 302, 304. A power source 306 is provided to the controller 303. An optional tamper sensor (not shown) is also provided to the controller 303.

When relaying sensor data to the base unit 112, the controller 303 receives data from the first transceiver 302 and provides the data to the second transceiver 304. When relaying instructions from the base unit 112 to a sensor unit, the controller 303 receives data from the second transceiver 304 and provides the data to the first transceiver 302. In one embodiment, the controller 303 conserves power by powering-down the transceivers 302, 304 during periods when the controller 303 is not expecting data. The controller 303 also monitors the power source 306 and provides status information, such as, for example, self-diagnostic information and/or information about the health of the power source 306, to the base unit 112. In one embodiment, the controller 303 sends status information to the base unit 112 at regular intervals. In one embodiment, the controller 303 sends status information to the base unit 112 when requested by the base unit 112. In one embodiment, the controller 303 sends status information to the base unit 112 when a fault condition (e.g., battery low) is detected.

In one embodiment, the controller 303 includes a table or list of identification codes for wireless sensor units 102. The repeater 303 forwards packets received from, or sent to, sensor units 102 in the list. In one embodiment, the repeater 110 receives entries for the list of sensor units from the computer 113. In one embodiment, the controller 303 determines when a transmission is expected from the sensor units 102 in the table of sensor units and places the repeater 110 (e.g., the transceivers 302, 304) in a low-power mode when no transmissions are expected from the transceivers on the list. In one embodiment, the controller 303 recalculates the times for low-power operation when a command to change reporting interval is forwarded to one of the sensor units 102 in the list (table) of sensor units or when a new sensor unit is added to the list (table) of sensor units.

Figure 4:
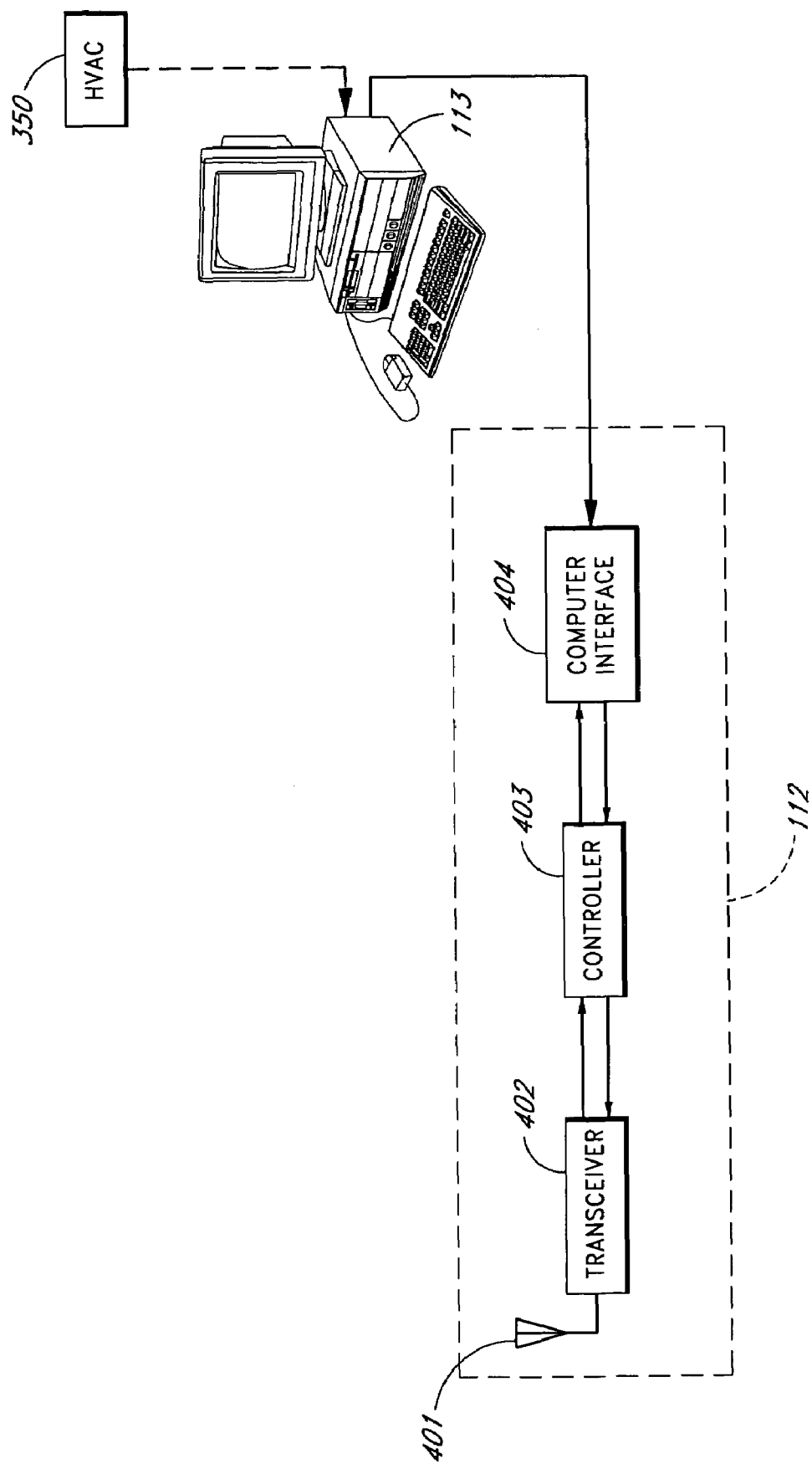
FIG. 4 is a block diagram of the base unit.

FIG. 4 is a block diagram of the base unit 112. In the base unit 112, a transceiver 402 and a computer interface 404 are provided to a controller 403. The controller 303 typically provides data and control information to the transceivers 402 and to the interface. The interface 404 is provided to a port on the monitoring computer 113. The interface 404 can be a standard computer data interface, such as, for example, Ethernet, wireless Ethernet, firewire port, Universal Serial Bus (USB) port, Bluetooth, etc.

Figure 5:
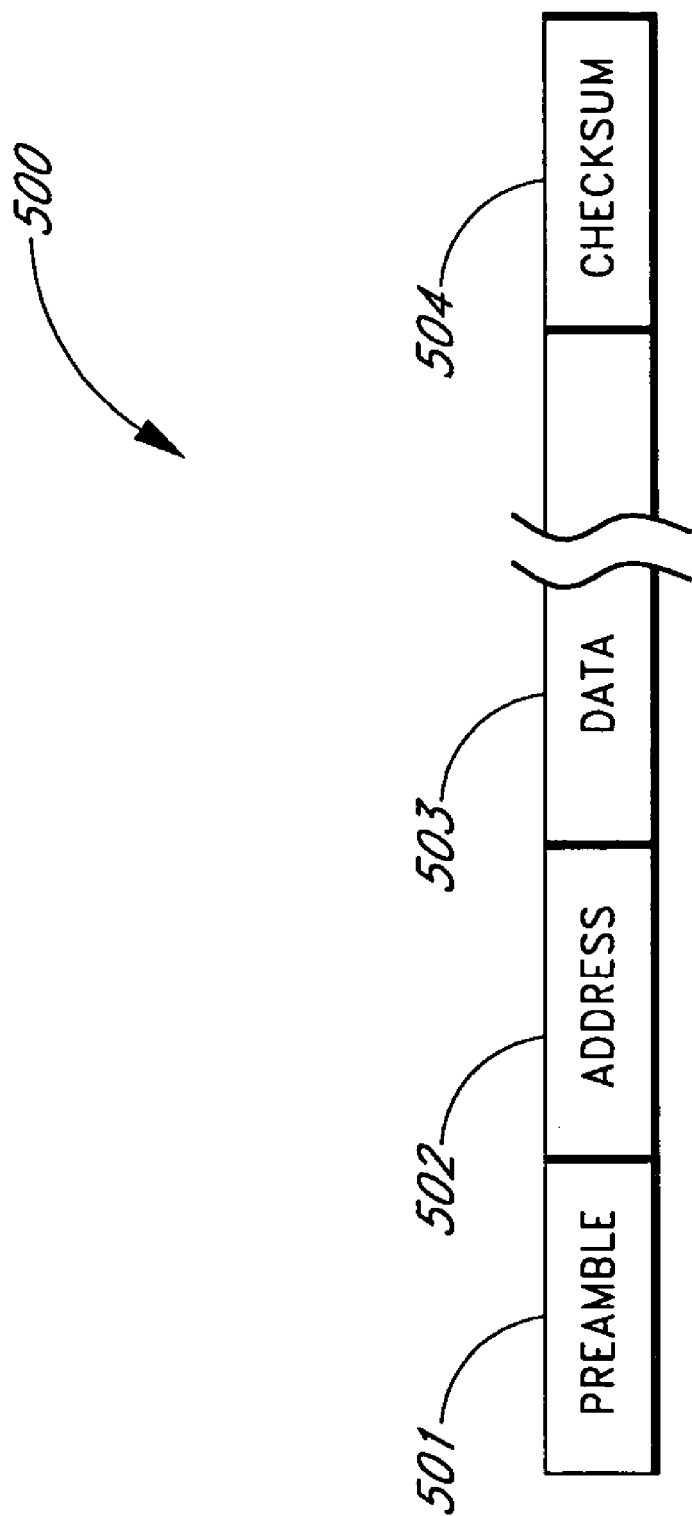
FIG. 5 shows a network communication packet used by the sensor units, repeater units, base unit, and PMU.

FIG. 5 shows one embodiment of a communication packet 500 used by the sensor units, repeater units, base unit, and PMU. The packet 500 includes a preamble portion 501, an address (or ID) portion 502, a data payload portion 503, and an integrity portion 504. In one embodiment, the integrity portion 504 includes a checksum. In one embodiment, the sensor units 102-106, the repeater units 110-111, and the base unit 112 communicate using packets such as the packet 500. In one embodiment, the packets 500 are transmitted using FHSS.

In one embodiment, the data packets that travel between the sensor unit 102, the repeater unit 111, the base unit 112, and the PMU 125 are encrypted. In one embodiment, the data packets that travel between the sensor unit 102, the repeater unit 111, the base unit 112, and the PMU 125 are encrypted and an authentication code is provided in the data packet so that the sensor unit 102, the repeater unit, and/or the base unit 112 can verify the authenticity of the packet.

In one embodiment the address portion 502 includes a first code and a second code. In one embodiment, the repeater 111 only examines the first code to determine if the packet should be forwarded. Thus, for example, the first code can be interpreted as a building (or building complex) code and the second code interpreted as a subcode (e.g., an apartment code, area code, etc.). A repeater that uses the first code for forwarding, thus, forwards packets having a specified first code (e.g., corresponding to the repeater's building or building complex). Thus, alleviates the need to program a list of sensor units 102 into a repeater, since a group of sensors in a building will typically all have the same first code but different second codes. A repeater so configured, only needs to know the first code to forward packets for any repeater in the building or building complex. This does, however, raise the possibility that two repeaters in the same building could try to forward packets for the same sensor unit 102. In one embodiment, each repeater waits for a programmed delay period before forwarding a packet. Thus, reducing the chance of packet collisions at the base unit (in the case of sensor unit to base unit packets) and reducing the chance of packet collisions at the sensor unit (in the case of base unit to sensor unit packets). In one embodiment, a delay period is programmed into each repeater. In one embodiment, delay periods are pre-programmed onto the repeater units at the factory or during installation. In one embodiment, a delay period is programmed into each repeater by the base unit 112. In one embodiment, a repeater randomly chooses a delay period. In one embodiment, a repeater randomly chooses a delay period for each forwarded packet. In one embodiment, the first code is at least 6 digits. In one embodiment, the second code is at least 5 digits.

In one embodiment, the first code and the second code are programmed into each sensor unit at the factory. In one embodiment, the first code and the second code are programmed when the sensor unit is installed. In one embodiment, the base unit 112 can re-program the first code and/or the second code in a sensor unit.

In one embodiment, collisions are further avoided by configuring each repeater unit 111 to begin transmission on a different frequency channel. Thus, if two repeaters attempt to begin transmission at the same time, the repeaters will not interfere with each other because the transmissions will begin on different channels (frequencies).

Figure 6:
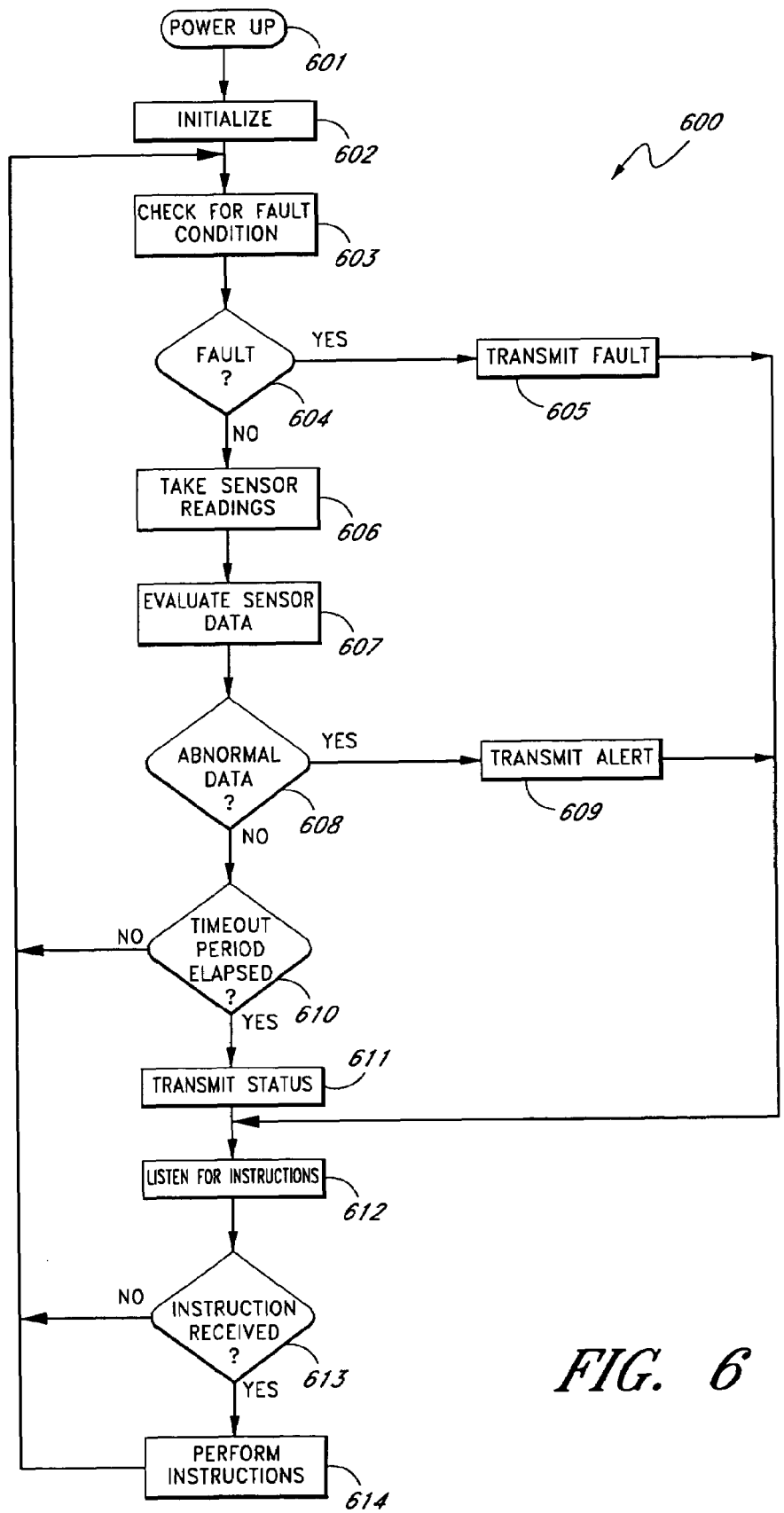
FIG. 6 is a flowchart showing operation of a sensor unit that provides relatively continuous monitoring.

FIG. 6 is a flowchart showing one embodiment of the operation of the sensor unit 102 wherein relatively continuous monitoring is provided. In FIG. 6, a power up block 601 is followed by an initialization block 602. After initialization, the sensor unit 102 checks for a fault condition (e.g., activation of the tamper sensor, low battery, internal fault, etc.) in a block 603. A decision block 604 checks the fault status. If a fault has occurred, then the process advances to a block 605 were the fault information is transmitted to the repeater 110 (after which, the process advances to a block 612); otherwise, the process advances to a block 606. In the block 606, the sensor unit 102 takes a sensor reading from the sensor(s) 201. The sensor data is subsequently evaluated in a block 607. If the sensor data is abnormal, then the process advances to a transmit block 609 where the sensor data is transmitted to the repeater 110 (after which, the process advances to a block 612); otherwise, the process advances to a timeout decision block 610. If the timeout period has not elapsed, then the process returns to the fault-check block 603; otherwise, the process advances to a transmit status block 611 where normal status information is transmitted to the repeater 110. In one embodiment, the normal status information transmitted is analogous to a simple "ping" which indicates that the sensor unit 102 is functioning normally. After the block 611, the process proceeds to a block 612 where the sensor unit 102 momentarily listens for instructions from the monitor computer 113. If an instruction is received, then the sensor unit 102 performs the instructions, otherwise, the process returns to the status check block 603. In one embodiment, transceiver 203 is normally powered down. The controller 202 powers up the transceiver 203 during execution of the blocks 605, 609, 611, and 612. The monitoring computer 113 can send instructions to the sensor unit 102 to change the parameters used to evaluate data used in block 607, the listen period used in block 612, etc.

Figure 7:
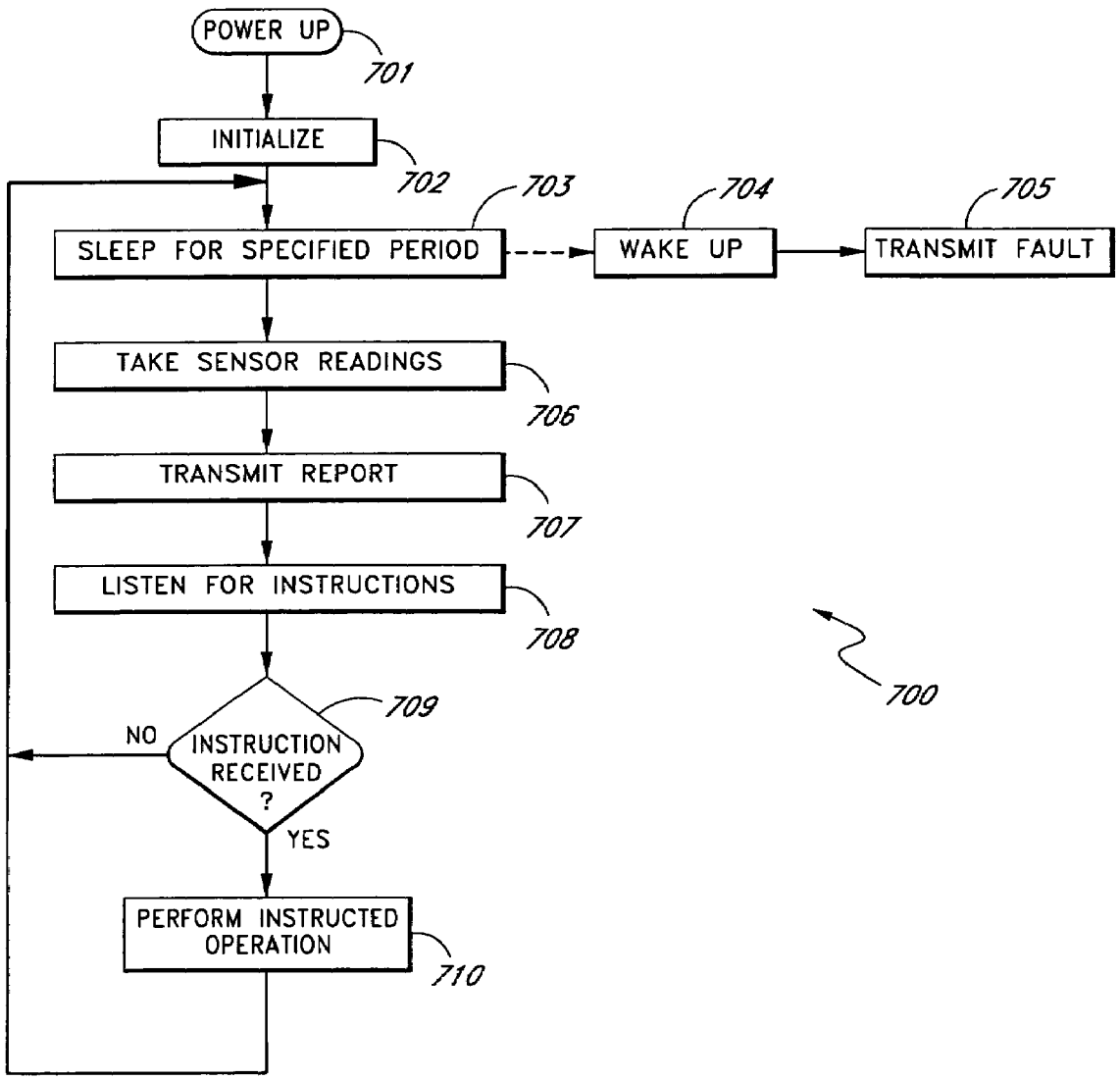
FIG. 7 is a flowchart showing operation of a sensor unit that provides periodic monitoring.

Relatively continuous monitoring, such as shown in FIG. 6, is appropriate for sensor units that sense relatively high-priority data (e.g., smoke, fire, carbon monoxide, flammable gas, etc.). By contrast, periodic monitoring can be used for sensors that sense relatively lower priority data (e.g., humidity, moisture, water usage, etc.). FIG. 7 is a flowchart showing one embodiment of operation of the sensor unit 102 wherein periodic monitoring is provided. In FIG. 7, a power up block 701 is followed by an initialization block 702. After initialization, the sensor unit 102 enters a low-power sleep mode. If a fault occurs during the sleep mode (e.g., the tamper sensor is activated), then the process enters a wake-up block 704 followed by a transmit fault block 705. If no fault occurs during the sleep period, then when the specified sleep period has expired, the process enters a block 706 where the sensor unit 102 takes a sensor reading from the sensor(s) 201. The sensor data is subsequently sent to the monitoring computer 113 in a report block 707. After reporting, the sensor unit 102 enters a listen block 708 where the sensor unit 102 listens for a relatively short period of time for instructions from monitoring computer 708. If an instruction is received, then the sensor unit 102 performs the instructions, otherwise, the process returns to the sleep block 703. In one embodiment, the sensor 201 and transceiver 203 are normally powered down. The controller 202 powers up the sensor 201 during execution of the block 706. The controller 202 powers up the transceiver during execution of the blocks 705, 707, and 708. The monitoring computer 113 can send instructions to the sensor unit 102 to change the sleep period used in block 703, the listen period used in block 708, etc.

In one embodiment, the sensor unit transmits sensor data until a handshaking-type acknowledgement is received. Thus, rather than sleep of no instructions or acknowledgements are received after transmission (e.g., after the decision block 613 or 709) the sensor unit 102 retransmits its data and waits for an acknowledgement. The sensor unit 102 continues to transmit data and wait for an acknowledgement until an acknowledgement is received. In one embodiment, the sensor unit accepts an acknowledgement from a repeater unit 111 and it then becomes the responsibility of the repeater unit 111 to make sure that the data is forwarded to the base unit 112. In one embodiment, the repeater unit 111 does not generate the acknowledgement, but rather forwards an acknowledgement from the base unit 112 to the sensor unit 102. The two-way communication ability of the sensor unit 102 provides the capability for the base unit 112 to control the operation of the sensor unit 102 and also provides the capability for robust handshaking-type communication between the sensor unit 102 and the base unit 112.

Regardless of the normal operating mode of the sensor unit 102 (e.g., using the Flowcharts of FIGS. 6, 7, or other modes) in one embodiment, the monitoring computer 113 can instruct the sensor unit 102 to operate in a relatively continuous mode where the sensor repeatedly takes sensor readings and transmits the readings to the monitoring computer 113. Such a mode would can be used, for example, when the sensor unit 102 (or a nearby sensor unit) has detected a potentially dangerous condition (e.g., smoke, rapid temperature rise, etc.)

Figure 8:
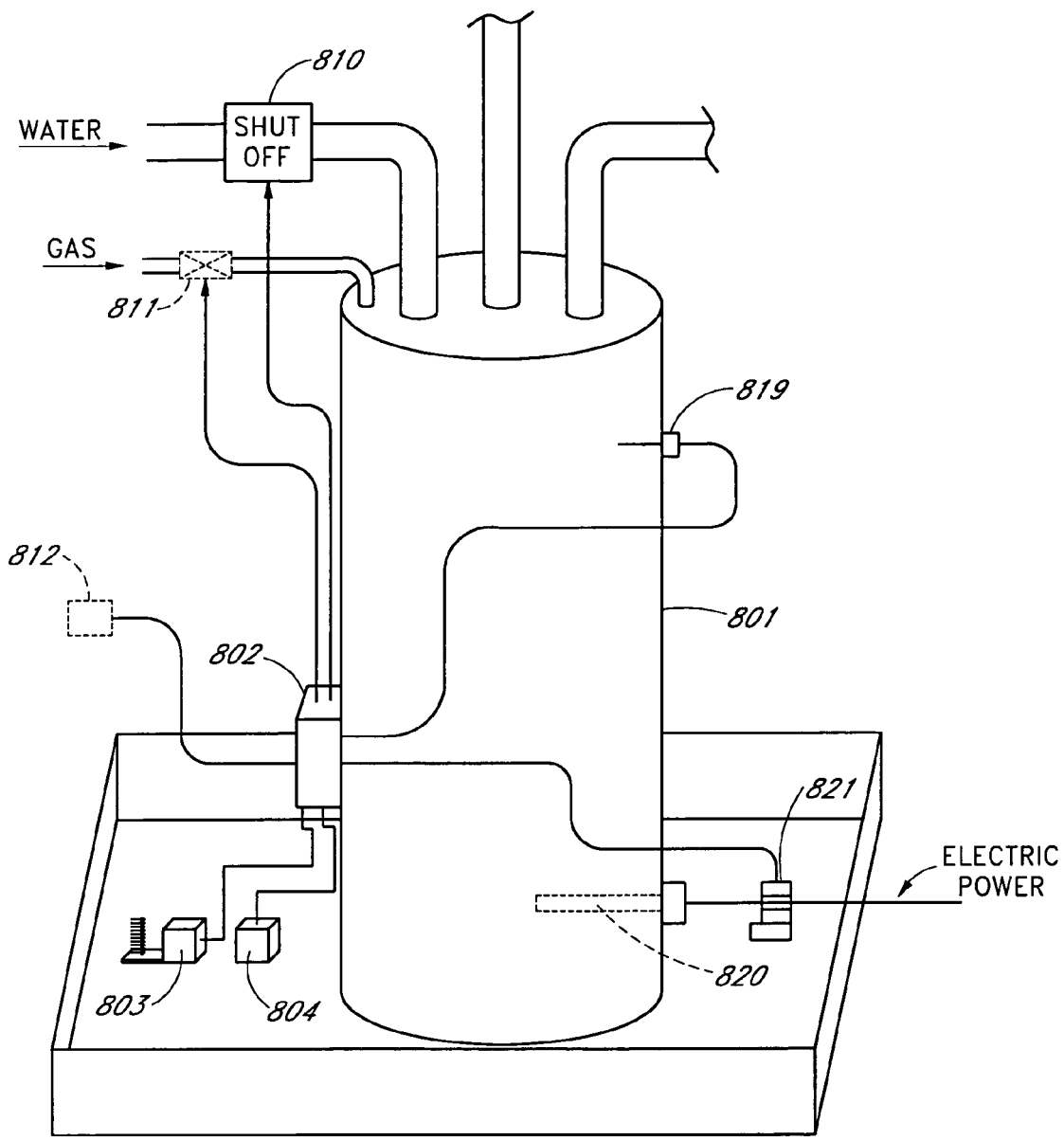
FIG. 8 shows how the sensor system can be used to detect water leaks.

FIG. 8 shows the sensor system used to detect water leaks. In one embodiment, the sensor unit 102 includes a water level sensor and 803 and/or a water temperature sensor 804. The water level sensor 803 and/or water temperature sensor 804 are place, for example, in a tray underneath a water heater 801 in order to detect leaks from the water heater 801 and thereby prevent water damage from a leaking water heater. In one embodiment, a temperature sensor is also provide to measure temperature near the water heater. The water level sensor can also be placed under a sink, in a floor sump, etc. In one embodiment, the severity of a leak is ascertained by the sensor unit 102 (or the monitoring computer 113) by measuring the rate of rise in the water level. When placed near the hot water tank 801, the severity of a leak can also be ascertained at least in part by measuring the temperature of the water. In one embodiment, a first water flow sensor is placed in an input water line for the hot water tank 801 and a second water flow sensor is placed in an output water line for the hot water tank. Leaks in the tank can be detected by observing a difference between the water flowing through the two sensors.

In one embodiment, a remote shutoff valve 810 is provided, so that the monitoring system 100 can shutoff the water supply to the water heater when a leak is detected. In one embodiment, the shutoff valve is controlled by the sensor unit 102. In one embodiment, the sensor unit 102 receives instructions from the base unit 112 to shut off the water supply to the heater 801. In one embodiment, the responsible party 120 sends instructions to the monitoring computer 113 instructing the monitoring computer 113 to send water shut off instructions to the sensor unit 102. Similarly, in one embodiment, the sensor unit 102 controls a gas shutoff valve 811 to shut off the gas supply to the water heater 801 and/or to a furnace (not shown) when dangerous conditions (such as, for example, gas leaks, carbon monoxide, etc.) are detected. In one embodiment, a gas detector 812 is provided to the sensor unit 102. In one embodiment, the gas detector 812 measures carbon monoxide. In one embodiment, the gas detector 812 measures flammable gas, such as, for example, natural gas or propane.

In one embodiment, an optional temperature sensor 818 is provided to measure stack temperature. Using data from the temperature sensor 818, the sensor unit 102 reports conditions, such as, for example, excess stack temperature. Excess stack temperature is often indicative of poor heat transfer (and thus poor efficiency) in the water heater 818.

In one embodiment, an optional temperature sensor 819 is provided to measure temperature of water in the water heater 810. Using data from the temperature sensor 819, the sensor unit 102 reports conditions, such as, for example, over-temperature or under-temperature of the water in the water heater.

In one embodiment, an optional current probe 821 is provided to measure electric current provided to a heating element 820 in an electric water heater. Using data from the current probe 821, the sensor unit 102 reports conditions, such as, for example, no current (indicating a burned-out heating element 820). An over-current condition often indicates that the heating element 820 is encrusted with mineral deposits and needs to be replaced or cleaned. By measuring the current provided to the water heater, the monitoring system can measure the amount of energy provided to the water heater and thus the cost of hot water, and the efficiency of the water heater.

In one embodiment, the sensor 803 includes a moisture sensor. Using data from the moisture sensor, the sensor unit 102 reports moisture conditions, such as, for example, excess moisture that would indicate a water leak, excess condensation, etc.

In one embodiment, the sensor unit 102 is provided to a moisture sensor (such as the sensor 803) located near an air conditioning unit. Using data from the moisture sensor, the sensor unit 102 reports moisture conditions, such as, for example, excess moisture that would indicate a water leak, excess condensation, etc.

In one embodiment, the sensor 201 includes a moisture sensor. The moisture sensor can be place under a sink or a toilet (to detect plumbing leaks) or in an attic space (to detect roof leaks).

Excess humidity in a structure can cause severe problems such as rotting, growth of molds, mildew, and fungus, etc. (hereinafter referred to generically as fungus). In one embodiment, the sensor 201 includes a humidity sensor. The humidity sensor can be place under a sink, in an attic space, etc. to detect excess humidity (due to leaks, condensation, etc.). In one embodiment, the monitoring computer 113 compares humidity measurements taken from different sensor units in order to detect areas that have excess humidity. Thus, for example, the monitoring computer 113 can compare the humidity readings from a first sensor unit 102 in a first attic area, to a humidity reading from a second sensor unit 102 in a second area. For example, the monitoring computer can take humidity readings from a number of attic areas to establish a baseline humidity reading and then compare the specific humidity readings from various sensor units to determine if one or more of the units are measuring excess humidity. The monitoring computer 113 would flag areas of excess humidity for further investigation by maintenance personnel. In one embodiment, the monitoring computer 113 maintains a history of humidity readings for various sensor units and flags areas that show an unexpected increase in humidity for investigation by maintenance personnel.

In one embodiment, the monitoring system 100 detects conditions favorable for fungus (e.g., mold, mildew, fungus, etc.) growth by using a first humidity sensor located in a first building area to produce first humidity data and a second humidity sensor located in a second building area to produce second humidity data. The building areas can be, for example, areas near a sink drain, plumbing fixture, plumbing, attic areas, outer walls, a bilge area in a boat, etc.

The monitoring station 113 collects humidity readings from the first humidity sensor and the second humidity sensor and indicates conditions favorable for fungus growth by comparing the first humidity data and the second humidity data. In one embodiment, the monitoring station 113 establishes a baseline humidity by comparing humidity readings from a plurality of humidity sensors and indicates possible fungus growth conditions in the first building area when at least a portion of the first humidity data exceeds the baseline humidity by a specified amount. In one embodiment, the monitoring station 113 establishes a baseline humidity by comparing humidity readings from a plurality of humidity sensors and indicates possible fungus growth conditions in the first building area when at least a portion of the first humidity data exceeds the baseline humidity by a specified percentage.

In one embodiment, the monitoring station 113 establishes a baseline humidity history by comparing humidity readings from a plurality of humidity sensors and indicates possible fungus growth conditions in the first building area when at least a portion of the first humidity data exceeds the baseline humidity history by a specified amount over a specified period of time. In one embodiment, the monitoring station 113 establishes a baseline humidity history by comparing humidity readings from a plurality of humidity sensors over a period of time and indicates possible fungus growth conditions in the first building area when at least a portion of the first humidity data exceeds the baseline humidity by a specified percentage of a specified period of time.

In one embodiment, the sensor unit 102 transmits humidity data when it determines that the humidity data fails a threshold test. In one embodiment, the humidity threshold for the threshold test is provided to the sensor unit 102 by the monitoring station 113. In one embodiment, the humidity threshold for the threshold test is computed by the monitoring station from a baseline humidity established in the monitoring station. In one embodiment, the baseline humidity is computed at least in part as an average of humidity readings from a number of humidity sensors. In one embodiment, the baseline humidity is computed at least in part as a time average of humidity readings from a number of humidity sensors. In one embodiment, the baseline humidity is computed at least in part as a time average of humidity readings from a humidity sensor. In one embodiment, the baseline humidity is computed at least in part as the lesser of a maximum humidity reading an average of a number of humidity readings.

In one embodiment, the sensor unit 102 reports humidity readings in response to a query by the monitoring station 113. In one embodiment, the sensor unit 102 reports humidity readings at regular intervals. In one embodiment, a humidity interval is provided to the sensor unit 102 by the monitoring station 113.

In one embodiment, the calculation of conditions for fungus growth is comparing humidity readings from one or more humidity sensors to the baseline (or reference) humidity. In one embodiment, the comparison is based on comparing the humidity readings to a percentage (e.g., typically a percentage greater than 100%) of the baseline value. In one embodiment, the comparison is based on comparing the humidity readings to a specified delta value above the reference humidity. In one embodiment, the calculation of likelihood of conditions for fungus growth is based on a time history of humidity readings, such that the longer the favorable conditions exist, the greater the likelihood of fungus growth. In one embodiment, relatively high humidity readings over a period of time indicate a higher likelihood of fungus growth than relatively high humidity readings for short periods of time. In one embodiment, a relatively sudden increase in humidity as compared to a baseline or reference humidity is reported by the monitoring station 113 as a possibility of a water leak. If the relatively high humidity reading continues over time then the relatively high humidity is reported by the monitoring station 113 as possibly being a water leak and/or an area likely to have fungus growth or water damage.

Temperatures relatively more favorable to fungus growth increase the likelihood of fungus growth. In one embodiment, temperature measurements from the building areas are also used in the fungus grown-likelihood calculations. In one embodiment, a threshold value for likelihood of fungus growth is computed at least in part as a function of temperature, such that temperatures relatively more favorable to fungus growth result in a relatively lower threshold than temperatures relatively less favorable for fungus growth. In one embodiment, the calculation of a likelihood of fungus growth depends at least in part on temperature such that temperatures relatively more favorable to fungus growth indicate a relatively higher likelihood of fungus growth than temperatures relatively less favorable for fungus growth. Thus, in one embodiment, a maximum humidity and/or minimum threshold above a reference humidity is relatively lower for temperature more favorable to fungus growth than the maximum humidity and/or minimum threshold above a reference humidity for temperatures relatively less favorable to fungus growth.

In one embodiment, a water flow sensor is provided to the sensor unit 102. The sensor unit 102 obtains water flow data from the water flow sensor and provides the water flow data to the monitoring computer 113. The monitoring computer 113 can then calculate water usage. Additionally, the monitoring computer can watch for water leaks, by, for example, looking for water flow when there should be little or no flow. Thus, for example, if the monitoring computer detects water usage throughout the night, the monitoring computer can raise an alert indicating that a possible water leak has occurred.

In one embodiment, the sensor 201 includes a water flow sensor is provided to the sensor unit 102. The sensor unit 102 obtains water flow data from the water flow sensor and provides the water flow data to the monitoring computer 113. The monitoring computer 113 can then calculate water usage. Additionally, the monitoring computer can watch for water leaks, by, for example, looking for water flow when there should be little or no flow. Thus, for example, if the monitoring computer detects water usage throughout the night, the monitoring computer can raise an alert indicating that a possible water leak has occurred.

In one embodiment, the sensor 201 includes a fire-extinguisher tamper sensor is provided to the sensor unit 102. The fire-extinguisher tamper sensor reports tampering with or use of a fire-extinguisher. In one embodiment the fire-extinguisher temper sensor reports that the fire extinguisher has been removed from its mounting, that a fire extinguisher compartment has been opened, and/or that a safety lock on the fire extinguisher has been removed.

In one embodiment, the sensor unit 102 is configured as an adjustable-threshold sensor that computes a threshold level. In one embodiment, the threshold is computed as an average of a number of sensor measurements. In one embodiment, the average value is a relatively long-term average. In one embodiment, the average is a time-weighted average wherein recent sensor readings used in the averaging process are weighted differently than less recent sensor readings. In one embodiment, more recent sensor readings are weighted relatively more heavily than less recent sensor readings. In one embodiment, more recent sensor readings are weighted relatively less heavily than less recent sensor readings. The average is used to set the threshold level. When the sensor readings rise above the threshold level, the sensor indicates a notice condition. In one embodiment, the sensor indicates a notice condition when the sensor reading rises above the threshold value for a specified period of time. In one embodiment, the sensor indicates a notice condition when a statistical number of sensor readings (e.g., 3 of 2, 5 of 3, 10 of 7, etc.) are above the threshold level. In one embodiment, the sensor unit 102 indicates various levels of alarm (e.g., warning, alert, alarm) based on how far above the threshold the sensor reading has risen.

In one embodiment, the sensor unit 102 computes the notice level according to how far the sensor readings have risen above the threshold and how rapidly the sensor readings have risen. For example, for purposes of explanation, the level of readings and the rate of rise can be quantified as low, medium, and high. The combination of sensor reading level and rate of rise then can be show as a table, as show in Table 1. Table 1 provides examples and is provided by way of explanation, not limitation.

TABLE 1

| | Sensor Reading Level (as compared to the threshold) | | | |
|---|---|---|---|---|
| Rate | High | Warning | Alarm | Alarm |
| of Rise | Medium | Notice | Warning | Alarm |
| | Low | Notice | Warning | Alarm |
| | Low | | Medium | High |

One of ordinary skill in the art will recognize that the notice level N can be expressed as an equation N=ƒ(t, v, r), where t is the threshold level, v is the sensor reading, and r is the rate of rise of the sensor reading. In one embodiment, the sensor reading v and/or the rate of rise r are lowpass filtered in order to reduce the effects of noise in the sensor readings. In one embodiment, the threshold is computed by lowpass filtering the sensor readings v using a filter with a relatively low cutoff frequency. A filter with a relatively low cutoff frequency produces a relatively long-term averaging effect. In one embodiment, separate thresholds are computed for the sensor reading and for the rate of rise.

In one embodiment, a calibration procedure period is provided when the sensor unit 102 is powered up. During the calibration period, the sensor data values from the sensor 201 are used to compute the threshold value, but the sensor does not compute notices, warnings, alarms, etc., until the calibration period is complete. In one embodiment, the sensor unit 102 uses a fixed (e.g., pre-programmed) threshold value to compute notices, warnings, and alarms during the calibration period and then uses the adjustable threshold value once the calibration period has ended.

In one embodiment, the sensor unit 102 determines that a failure of the sensor 201 has occurred when the adjustable threshold value exceeds a maximum adjustable threshold value. In one embodiment, the sensor unit 102 determines that a failure of the sensor 201 has occurred when the adjustable threshold value falls below a minimum adjustable threshold value. The sensor unit 102 can report such failure of the sensor 201 to the base unit 112.

In one embodiment, the sensor unit 102 obtains a number of sensor data readings from the sensor 201 and computes the threshold value as a weighted average using a weight vector. The weight vector weights some sensor data readings relatively more than other sensor data readings.

In one embodiment, the sensor unit 102 obtains a number of sensor data readings from the sensor unit 201 and filters the sensor data readings and calculates the threshold value from the filtered sensor data readings. In one embodiment, the sensor unit applies a lowpass filter. In one embodiment, the sensor unit 201 uses a Kalman filter to remove unwanted components from the sensor data readings. In one embodiment, the sensor unit 201 discards sensor data readings that are "outliers" (e.g., too far above or too far below a normative value). In this manner, the sensor unit 102 can compute the threshold value even in the presence of noisy sensor data.

In one embodiment, the sensor unit 102 indicates a notice condition (e.g., alert, warning, alarm) when the threshold value changes too rapidly. In one embodiment, the sensor unit 102 indicates a notice condition (e.g., alert, warning, alarm) when the threshold value exceeds a specified maximum value. In one embodiment, the sensor unit 102 indicates a notice condition (e.g., alert, warning, alarm) when the threshold value falls below a specified minimum value.

In one embodiment, the sensor unit 102 adjusts one or more operating parameters of the sensor 201 according the threshold value. Thus, for example, in the example of an optical smoke sensor, the sensor unit 201 can reduce the power used to drive the LED in the optical smoke sensor when the threshold value indicates that the optical smoke sensor can be operated at lower power (e.g., low ambient light conditions, clean sensor, low air particulate conditions, etc.). The sensor unit 201 can increase the power used to drive the LED when the threshold value indicates that the optical smoke sensor should be operated at higher power (e.g., high ambient light, dirty sensor, higher particulates in the air, etc.).

In one embodiment, an output from a Heating Ventilating and/or Air Conditioning (HVAC) system 350 is optionally provided to the sensor unit 102 as shown in FIG. 2. In one embodiment, an output from the HVAC system 350 is optionally provided to the repeater 110 as shown in FIG. 3 and/or to the monitoring system 113 as shown in FIG. 4. In this manner, the system 100 is made aware of the operation of the HVAC system. When the HVAC system turns on or off, the airflow patterns in the room change, and thus the way in which smoke or other materials (e.g., flammable gases, toxic gases, etc.) changes as well. Thus, in one embodiment, the threshold calculation takes into account the airflow effects caused by the HVAC system. In one embodiment, an adaptive algorithm is used to allow the sensor unit 102 (or monitoring system 113) to "learn" how the HVAC system affects sensor readings and thus the sensor unit 102 (or monitoring system 113) can adjust the threshold level accordingly. In one embodiment, the threshold level is temporarily changed for a period of time (e.g., raised or lowered) to avoid false alarms when the HVAC system turns on or off. Once the airflow patterns in the room have re-adjusted to the HVAC state, then the threshold level can be re-established for desired system sensitivity.

Thus, for example, in one embodiment where an averaging or lowpass filter type process is used to establish the threshold level, the threshold level is temporarily set to de-sensitize the sensor unit 102 when the HVAC system turns on or off, thus allowing the averaging or lowpass filtering process to establish a new threshold level. Once a new threshold level is established (or after a specified period of time), then the sensor unit 102 returns to its normal sensitivity based on the new threshold level.

In one embodiment, the sensor 201 is configured as an infrared sensor. In one embodiment, the sensor 201 is configured as an infrared sensor to measure a temperature of objects within a field of view of the sensor 201. In one embodiment, the sensor 201 is configured as an infrared sensor. In one embodiment, the sensor 201 is configured as an infrared sensor to detect flames within a field of view of the sensor 201. In one embodiment, the sensor 201 is configured as an infrared sensor.

In one embodiment, the sensor 201 is configured as an imaging sensor. In one embodiment, the controller 202 is configured to detect flames by processing of image data from the imaging sensor.

Figure 9:
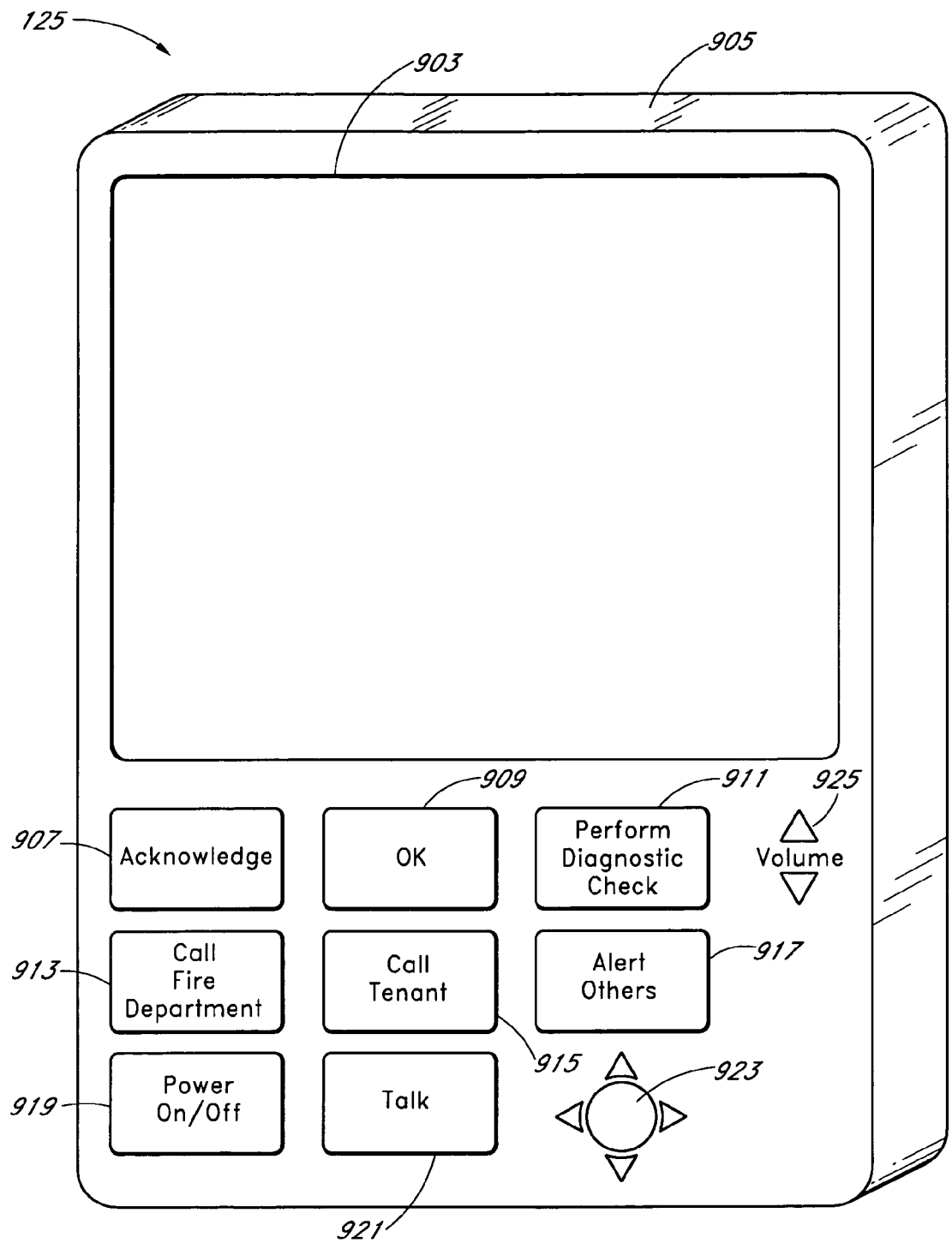
FIG. 9 shows an example of one embodiment of a PMU.

FIG. 9 shows an example of one embodiment of a PMU. The PMU 125 includes a PMU housing 905 covering electronic components (not shown). A screen 903 is attached to the front of PMU casing 905. PMU casing 905 can also optionally have PMU function keys such as, for example, ACKNOWLEDGE button 907, OK button 909, PERFORM DIAGNOSTIC CHECK button 911, CALL FIRE DEPARTMENT button 913, CALL TENANT button 915, ALERT OTHERS button 917, POWER ON/OFF button 919 and TALK button 921 as well as cursor controller 923 and volume controller 925.

The screen 903 can be in color or monotone. The screen 903 can have back lights in order to allow viewing in the dark. The screen 903 can be any screen used for displaying an electronic signal such as, for example, LCD, LED, color LCD, etc. In one embodiment, the screen 903 can replace one or all of the buttons through the use of a touch screen display. In one embodiment, the PMU 125 can use voice recognition in addition to, or instead of the buttons. In one embodiment, the PMU 125 can use a combination of touch screen display, buttons, and voice recognition.

In one embodiment, the PMU function keys can include an ACKNOWLEDGE button 907, an OK button 909, a PERFORM DIAGNOSTIC CHECK button 911, a CALL FIRE DEPARTMENT button 913, a CALL TENANT button 915, an ALERT OTHERS button 917, a POWER ON/OFF button 919, or a TALK BUTTON 921. PMU function keys can also include other control keys that would be useful in a building or complex monitoring system 113. The PMU function keys can be located in any convenient location on the PMU casing 905, and can be of any color, shape, size, or material. In addition, any combination, including only one or none of the PMU function keys can be incorporated into a PMU 125.

The ACKNOWLEDGE button 907 instructs the PMU 125 to send a response back to the monitoring computer 113 that the user has acknowledged receipt of the communication. The OK button 909 instructs the PMU 125 to send a response back to the monitoring computer 113 that the user has investigated the situation has determined that the situation is a false alarm or is resolved. The CALL FIRE DEPARTMENT button 913 instructs the PMU 125 to send a response back to the monitoring computer 113 instructing the monitoring computer 113 to call the local fire department and request assistance. In one embodiment, the CALL FIRE DEPARTMENT button 913 can also instruct the PMU 125 to connect the user directly to the fire department through a secondary transceiver 1313 configured to make regular telephone or cellular calls. In one embodiment, the CALL FIRE DEPARTMENT button 913 can instruct the PMU 125 to send a response to the monitoring computer 113 to call the fire department and to connect the PMU 125 to the fire department, so that the user can speak directly to the fire department without the need for a secondary transceiver 1313 in the PMU 125. In this embodiment, the monitoring computer 113 acts as a repeater between a telephone connection with the fire department and a radio frequency transmission, or other type of transmission from the PMU 125.

The CALL TENANT button 915 can instruct the PMU 125 to send an instruction to the monitoring computer 113 to call the tenant or occupant of the unit in which the sensor is located to see if the unit has occupants. In one embodiment, the CALL TENANT button 915 instructs the monitoring computer to call the occupants of the unit and then connect the PMU 125 device directly to the tenants through transceiver 1309. In one embodiment, the CALL TENANT button 915 instructs the PMU 125 to directly call the tenant through secondary transceiver 1313, thereby allowing the PMU user to talk directly with the tenant.

The ALERT OTHERS button 917 can instruct the PMU 125 to send an instruction to the monitoring computer 113 to contact other PMUs or other management through other devices (e.g. telephone, cell phone, fax, internet, etc.). In one embodiment, the ALERT OTHERS button 917 can also instruct the monitoring computer 113 to connect the PMU user to others (e.g., nearby apartments, other PMU users, management using other devices) that the monitoring computer contacts in order to discuss the situation. In one embodiment, the ALERT OTHERS button 917 can instruct the PMU 125 to directly contact other management through use of secondary transceiver 1313.

The POWER ON/OFF button 919 can instruct the PMU 125 to power up when it has been powered down, or alternatively to power down when it has been powered up in order to conserve energy. The TALK button 921 works in conjunction with a walkie talkie system that can be incorporated into the PMU 125. The TALK button 919 can either work in conjunction with the transceiver 1309, or with the secondary transceiver 1313. The TALK button 921 instructs the PMU 125 to send the electrical signal from the microphone 1303 to other local transceivers configured to receive the signal.

The CURSOR CONTROLLER button 923 can instruct the PMU 125 to move the curser on the screen either up or down or side to side in order to navigate through the entire message sent from the monitoring computer 113. In addition, the CURSOR CONTROLER button 923 can also allow a user to select certain information on the screen for additional use. The VOLUME button(s) 925 can be used to adjust the volume of the PMU 125.

The PERFORM DIAGNOSTIC CHECK button 911 instructs the PMU 125 to send a message to the monitoring computer 113 to run a diagnostic check on the sensor system. When the diagnostic check has been completed, the monitoring computer 113 then sends a communication to the PMU 125 containing the results of the diagnostic check.

In one embodiment, the PMU 125 can require the user to enter a password or pass code to identify the user. In this way, multiple users can use the same PMU. In addition, the monitoring computer 113 can also optionally be used to keep track of a user's movement throughout the day, as well as keeping a record of what the user's are doing. In one embodiment, different tasks can require different levels of clearance. For instance, a separate password or pass code can be required to program the sensors using the PMU 125.

Although FIG. 9 shows specific buttons, one of ordinary skill in the art will recognize that other buttons and/or a general keypad can be provided. In one embodiment, the screen 903 is used to provided menu options and the cursor controller 923 is used to navigate among the menu items and select menu items.

In one embodiment, the PMU 125 can be used to read the threshold level of various sensors and/or the sensor readings of the sensors. In one embodiment, when a sensor alert is sent to the PMU 125, the PMU 125 displays the sensor threshold level, and the sensor reading level (and/or the amount the sensor reading is above the threshold level.). In one embodiment, the PMU 125 displays a map of other sensors in the vicinity of the sensor sending the alert and the readings from the sensors in the vicinity of the sensor sending the alert.

In one embodiment, the user of the PMU 125 can select a sensor and change the sensor threshold value. Thus, for example, if a sensor is giving false alerts, the user of the PMU 125 can adjust the threshold level of the sensor to reduce the sensitivity of the sensor. Alternatively, if a first sensor in an apartment is sending an alert, the user of the PMU 125 can use the PMU 125 to change the threshold level (e.g., increase the sensitivity) of other sensors in the apartment or in nearby apartments.

In one embodiment the PMU 125 can display a map (e.g., a contour map, colorized map, etc.) of the sensors in the sensor system showing sensitivity, threshold value, battery value, sensor readings, etc. and thus provide the user with an overall picture of the sensor system.

Figure 10:
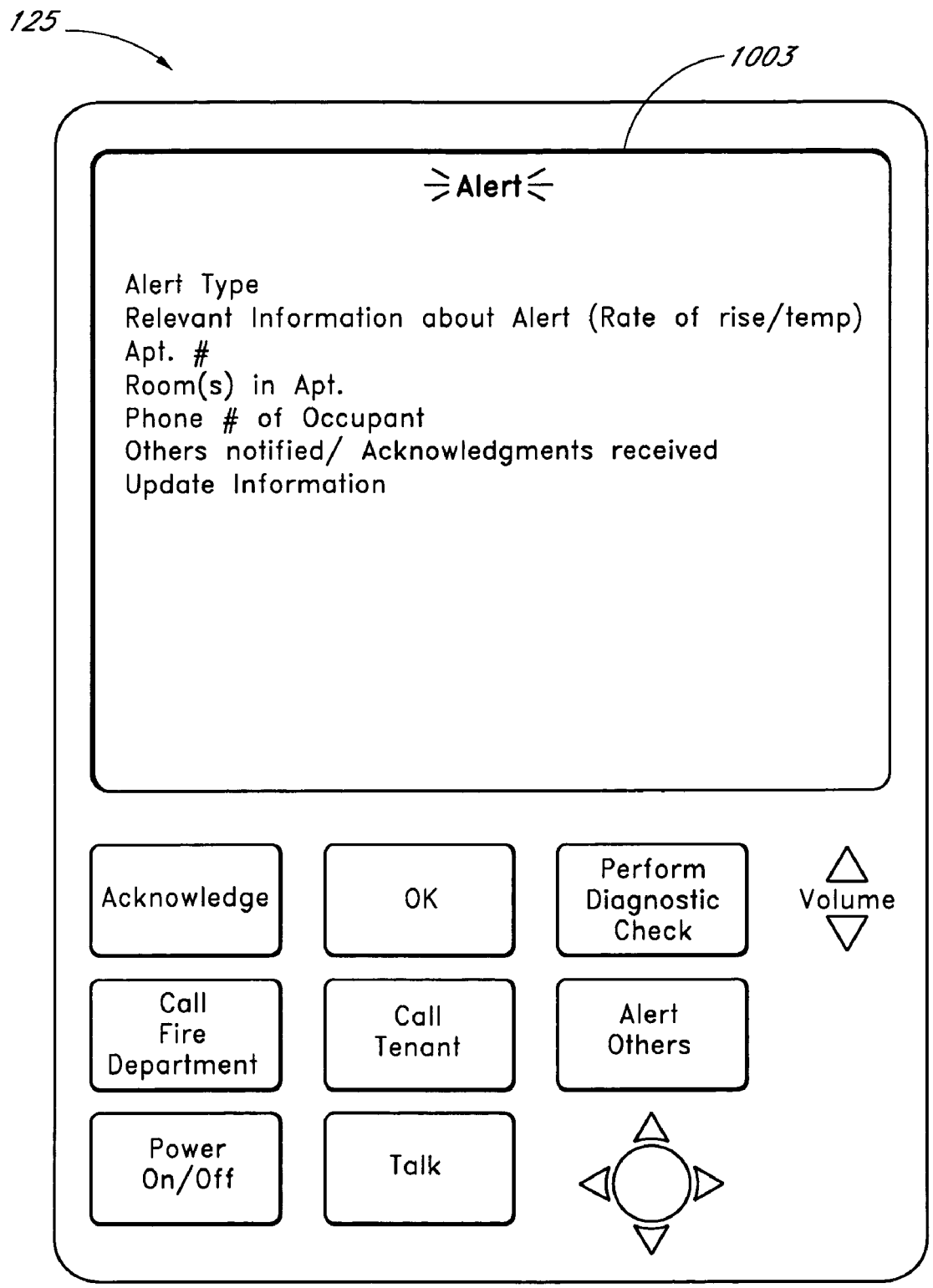
FIG. 10 shows a graphical representation of an alert of one embodiment.
Figure 11:
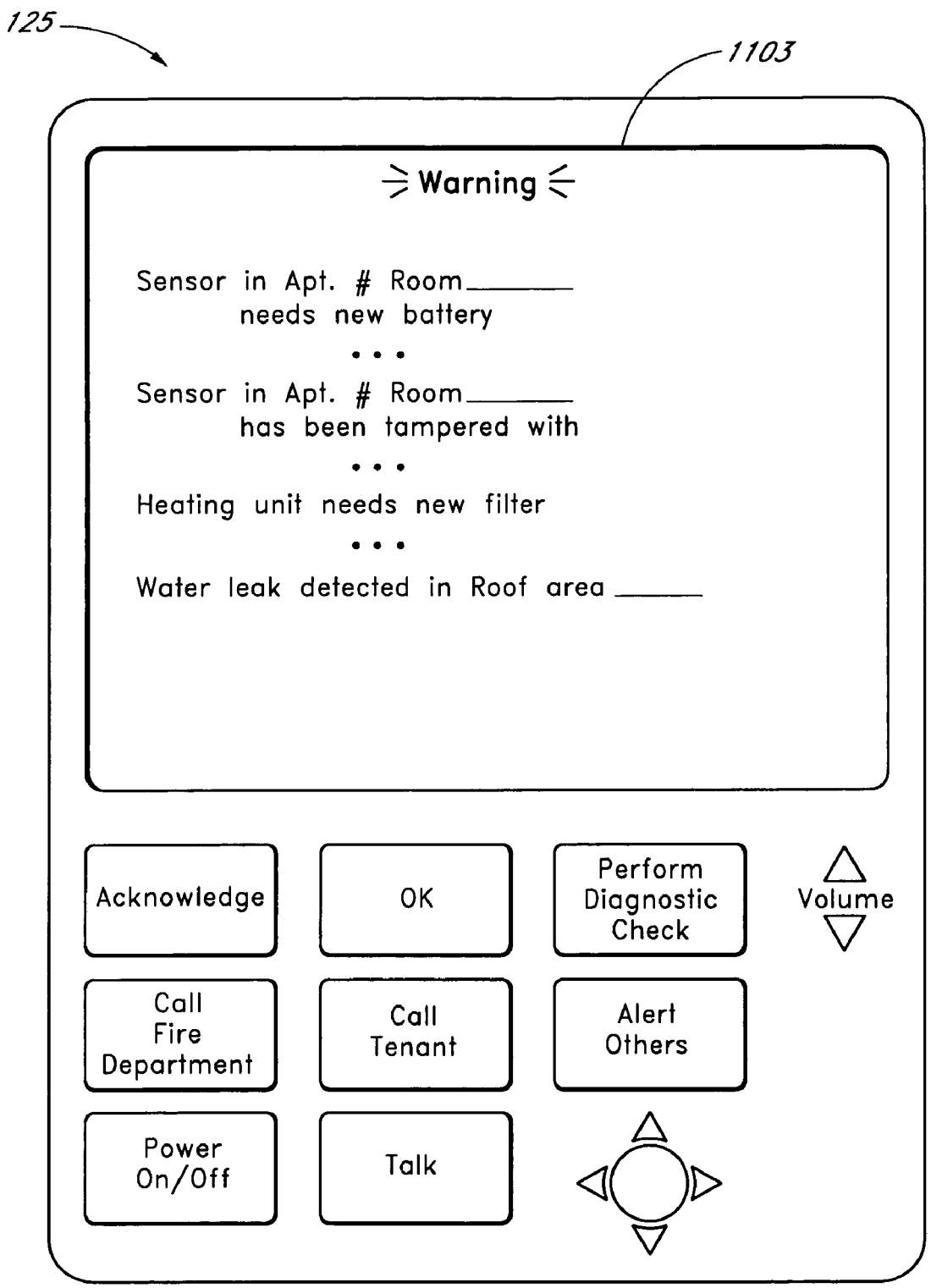
FIG. 11 shows a graphical representation of a warning of one embodiment.
Figure 12:
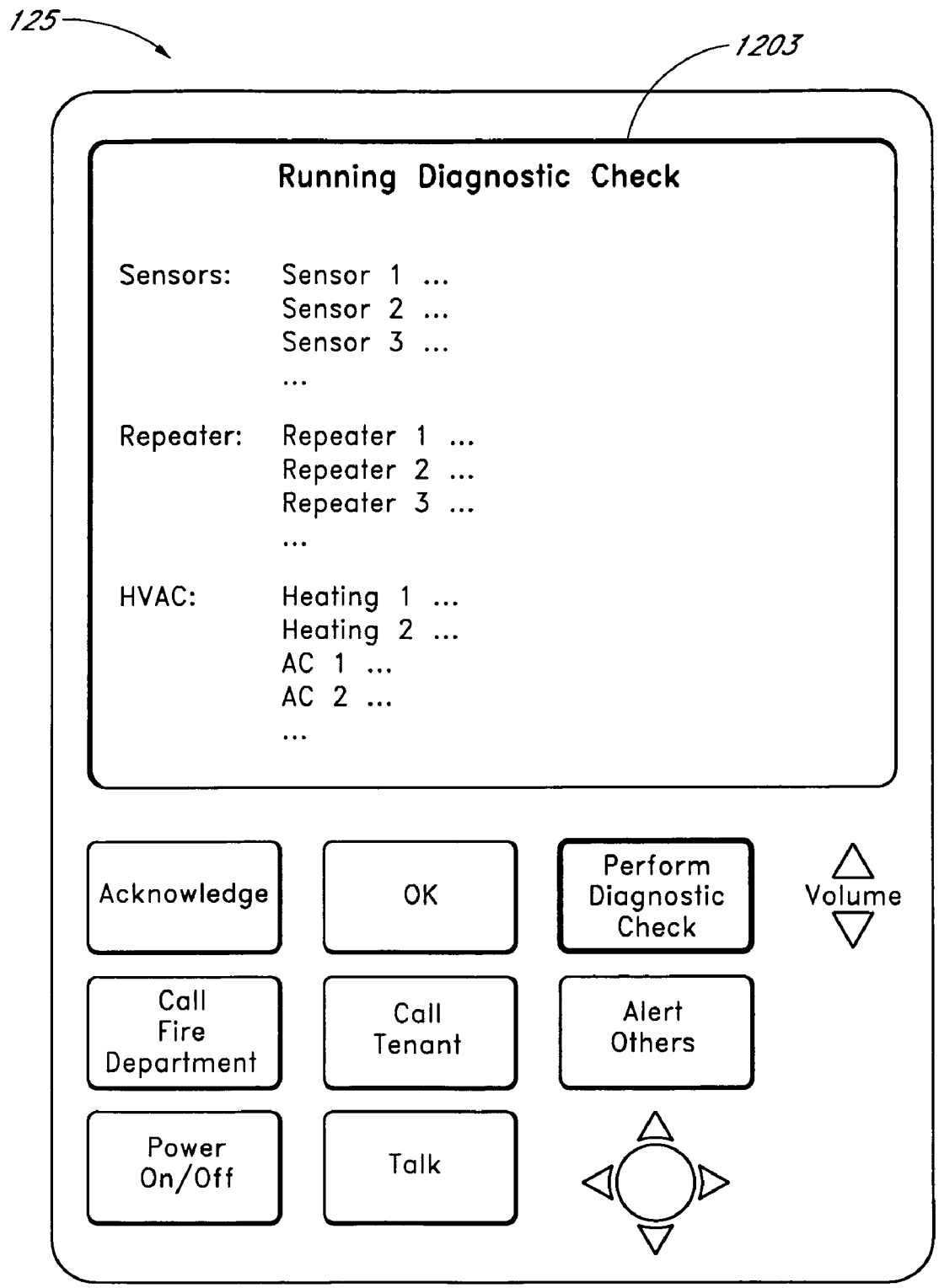
FIG. 12 shows a graphical representation of a diagnostic check of one embodiment.

FIGS. 10-12 show examples of various embodiments of communications received by the PMU 125. FIG. 10 graphically shows one embodiment of an alert message. The alert message is displayed on screen 1003 of PMU 125 and can include any relevant information about the alert. Relevant information can include any of the following: rate of rise of temperature or smoke, apartment number or unit number, which room(s) in the apartment the sensor(s) are located, the number of the sensors indicating an alert, the phone number of the occupants, whether or not others have been notified and/or whether others have acknowledged receipt of the notification, as well as any other update information relevant in assessing the situation.

FIG. 11 graphically shows one embodiment of a warning communication. The warning message can be displayed on screen 1103 of PMU 125. The warning message can contain information such as a sensor warning that it needs a new battery, a warning that a sensor has been tampered with, a warning that the heating, air conditioning or ventilation system needs maintenance or that a particular unit is not functioning properly, a warning that a water leak has been detected, or any other information relevant in maintaining a building or complex.

FIG. 12 graphically represents a communication in which a diagnostic check has been run. The diagnostic check can be displayed on screen 1203 of PMU 125. The diagnostic check communication can contain such information as the working status of each sensor, whether any maintenance is required on a sensor (e.g. needs new battery or is not functioning properly and needs repair or replacement). The diagnostic check can also contain information on the repeaters, the heating ventilation and air conditioning system, as well as diagnostic information on any other systems relevant in maintaining a building or complex.

Referring to FIGS. 10-12, the PMU 125 can indicate an alarm, warning, notice, or other communication. For instance, In one embodiment, an emergency alarm message can cause the PMU 125 to sound a loud beep, series of beeps, a horn, or any other noise designed to catch the attention of the user. In one embodiment, the PMU 125 can vibrate or flash lights to catch the attention of the user. In one embodiment, the PMU 125 can give an audible message, such as "SMOKE DETECTED IN APT. 33." Other types of communications, such as a warning, can be indicated in different ways, for instance a different type of audible sound. The volume of the auditory alerts can change depending on the severity of the condition. Different colors of lights can flash, or more or fewer lights can flash. In addition, the duration of the message indicators can be prolonged or shortened depending on the priority level of the condition.

Text displayed on the PMU screen 903 can also be suitably configured to convey the necessary information to building management. For instance, some or all of the words displayed on the screen can flash. Key words can be highlighted. For example, key information can be enlarged, bolded, displayed in different colors, or otherwise configured to grab the attention of the PMU user. In one embodiment, the screen can be too small to display all of the text of the message at the same time. In such cases, a cursor controller, such as cursor controller 923, can be used to scroll through the entirety of the message. Graphics can also be displayed on the screen along with the text or as a splash screen indicating the type of message that has been received before a user looks at the text of the message. In one embodiment, a user can be required to push a function key, such as ACKNOWLEDGE button 907 before the full text of the message is displayed on the screen. In addition, any advantageous modification to the text or graphics to be displayed can be incorporated into the display.

Figure 13:
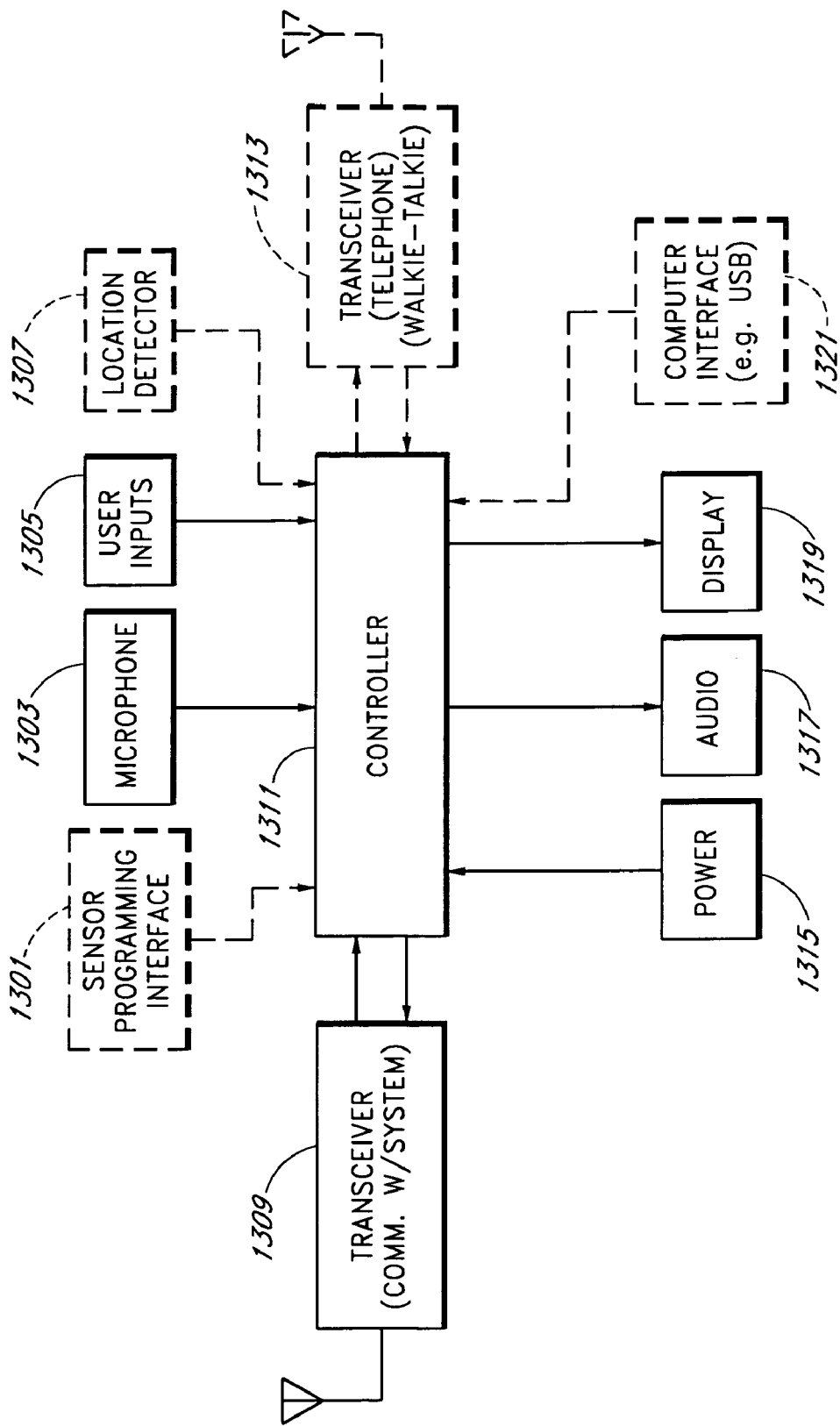
FIG. 13 is a block diagram of the PMU.

FIG. 13 is a block diagram of a PMU 125. In one embodiment, the PMU 125 includes a transceiver 1309 for communication between the sensor system and the controller 1311. The controller 1311 typically provides power, data, and control information to the transceiver 1309. A power source 1315 is provided to the controller 1311. The controller 1311 can also optionally receive and/or send electronic signals from a microphone 1303, user inputs 1305, a sensor programming interface 1301, a computer interface 1321, a location detector 1307, or a second transceiver 1313.

The microphone 1303 can be a microphone of any type which receives auditory noises and transmits an electronic signal representing the auditory noises. The user inputs 1305 can include any button or user input device for communicating an instruction to the controller 1311. The computer interface 1321 is used to provide communication between the PMU 125 and a computer system (e.g., the monitoring computer 113). The computer interface 1321 can be a standard computer data interface, such as, for example, Ethernet, wireless Ethernet, firewire port, Universal Serial Bus (USB) port, Bluetooth, etc. A location detector 1307 can provide location and/or movement details of the PMU 125. The location detector 1307 can be any location or motion sensing system, such as, for example, a Global Positioning System (GPS) or an accelerometer for detecting movement. A second transceiver 1313 can be provided for secondary communication channels. The second transceiver 1313 can communicate with any known communication network such as, for example, wireless Ethernet, cellular telephone, or Bluetooth.

The sensor programming interface 1301 can be used to enter or read programming information from the sensor units such as, for example, ID code, location code, software updates, etc. In one embodiment, the PMU programming interface 1301 can be designed to communicate to all the sensors in a sensor system at the same time. In one embodiment, the sensor programming interface 1301 can be designed so that the PMU 125 can communicate with a selected sensor or group of sensors. For instance, the sensor interface 1301 can be designed so that the PMU 125 must be close to the sensor in order to communicate with the sensor. This can be accomplished by designing the sensor programming interface 1301 with optical communications, such as, for example, an infra red (IR) transmitter, or designing the sensor programming interface 601 with a hardwire communication, such as through a wire connection directly with a sensor.

Figure 14:
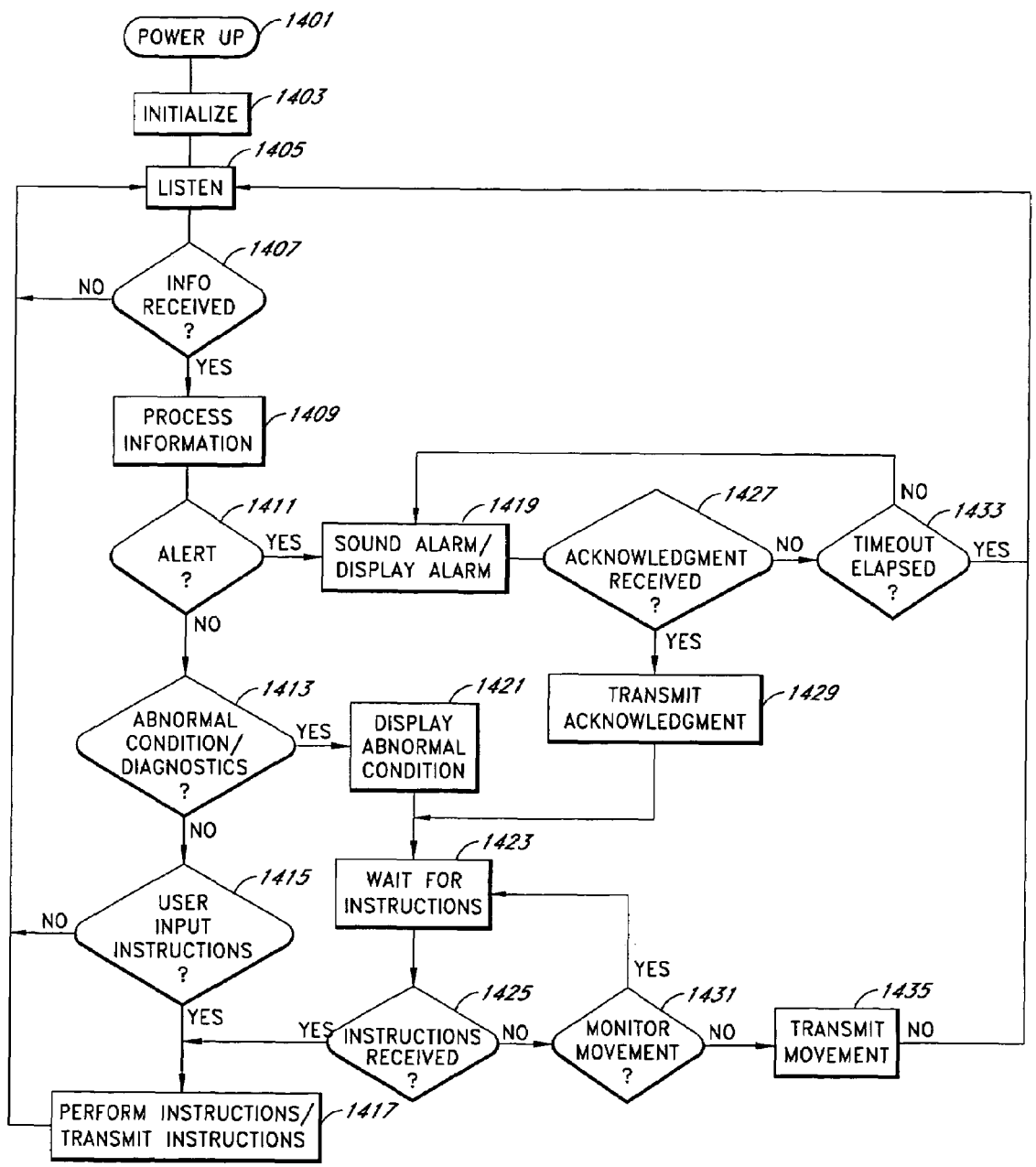
FIG. 14 is a flowchart showing the operation of a sensor system in communication with a PMU.

FIG. 14 is a flow chart of one embodiment showing how the PMU 125 communicates with the sensor system. The operation of the sensor system in communication with the PMU 125 begins at block 1401 where the PMU 125 is powered up. The PMU 125 next advances to block 1403 where the PMU 125 goes through an initialization (e.g. establishes communications with monitoring computer 113, uploads software, etc.). The PMU 125 then advances to block 1405 in which it listens for any communications from the monitoring computer 113. At block 1407, the PMU 125 decides whether information has been received. If information has been received, the PMU 125 advances to block 1409, otherwise, the PMU 125 goes back to block 1405 and listens for any communications. If information is received and the PMU 125 advances to block 1409, the PMU processes the information.

At decision block 1411, the PMU 125 decides if the information is an alert. If the information is an alert, then the PMU 125 advances to decision block 1419, otherwise, the PMU 125 advances to block 1413. At block 1413, the PMU 125 decides whether or not an abnormal condition communication or diagnostic check communication has been received. If there is an abnormal condition or diagnostic check, the PMU 125 advances to block 1421. Otherwise the PMU 125 advances to decision block 1415. At decision block 1415, the PMU 125 decides whether or not the user has inputted an instruction. If there has been a user-inputted instruction, then the PMU 125 moves on to block 1417, otherwise, it goes back to block 1405 and listens for the instruction. At block 1417, the PMU 125 performs the instruction or transmits the instructions back to the monitoring computer 113.

Returning now to block 1419, at block 1419 the PMU 125 sounds an alarm or displays an alarm and then advances to decision block 1427 where it looks to see if an acknowledgment has been received. If an acknowledgment has not been received, the PMU 125 advances to decision block 1433 where it looks to see if a timeout has elapsed. If a timeout has not elapsed, the PMU 125 moves back to 1419 where it sounds the alarm and waits for an acknowledgment. If a timeout has elapsed, the PMU 125 returns to block 1405 where it listens for instructions from the monitoring computer 113. If at block 1405 an acknowledgment has been received, the PMU 125 advances to block 1429 where it transmits the acknowledgment and then goes on to block 1423.

Returning now to block 1421, if an abnormal condition or diagnostic condition is received, then the PMU 125 displays the abnormal condition or diagnostic check message on the PMU screen 903 and then advances to block 1423. At block 1423, the PMU 125 waits for instructions. At decision block 1425, if an instruction is received, then the PMU 125 advances to block 1417. Otherwise, the PMU 125 advances to block 1431 where it monitors itself for movement. If there is no movement in the PMU 125, the PMU advances to block 1435 where it transmits a "no movement" alert to the monitoring computer and then returns to block 1405. If there has been movement, the PMU 125 returns to block 1423 and waits for instructions.

FIG. 15 is a graphical representation of alert priority responses by the monitoring computer 113. In one embodiment, different responses are assigned to different conditions. Priority levels can be based on level of smoke, gas, water, etc., the amount of time a sensor has been signaling, the rate of rise of smoke, temperature, gas, water, etc., the number of sensors signaling, or any other measurement that would be useful in assessing the priority level of the situation. For example, as shown in block 1501, if a low priority condition occurs, the monitoring computer 113 sends information about the condition to the PMU 125, and no further action is taken by the monitoring computer 113 with respect to communicating with the PMU 125. In an elevated priority condition, as shown in block 1503, the monitoring computer 113 sends information on the condition to the PMU 125 and then waits for acknowledgment and/or a response. If the monitoring computer 113 does not receive an acknowledgment or response, it will attempt to contact other PMUs or it can attempt to contact management through other channels (e.g. telephone, cell phone, fax, email, etc.). If the monitoring computer 113 receives an acknowledgement, but then receives a "no movement" alert from the PMU 125, the monitoring computer 113 will attempt to contact other PMUs or it can attempt to contact management through other channels. In a high priority condition, as shown in block 1505, the monitoring computer 113 can immediately send the information to multiple PMUs and can immediately attempt to contact management through other channels (e.g., telephone, cell phone, fax, email, etc.) and can wait a relatively short period of time for acknowledgment and responses before contacting the fire department directly. In a severe priority condition, as shown in block 1507, the monitoring computer can directly and immediately call the fire department and then can immediately attempt to contact all PMUs and all other management contacts. It will be understood by those of skill in the art that the responses and conditions of FIG. 15 are only one example and are not made by way of limitation. In addition, those of skill in the art that In one embodiment all conditions can be sent with the same priority level.

In one embodiment, neighboring unit occupants will also be notified of an occurring situation. For instance, in the case of a water leak, the occupants of the units located below the unit indicating a water leak would be notified that a unit above them has a water leak so that they can take precautions. Occupants of other units located above, below, adjacent to, or near a unit with a sensor signaling a situation can also be notified to the situation so that they can take appropriate precautions and/or provide more immediate assistance or help (e.g., water leak, fire/smoke detected, carbon monoxide detected, etc.). In one embodiment, the monitoring computer includes a database indicating the relative locations of the various sensor units 102 so that the monitoring computer 113 it knows which units to notify in the event a situation does occur. Thus, for example, the monitoring computer can be programmed so that it knows units 201 and 101 are below unit 301, or that unit 303 is adjacent to unit 301 and unit 302 is across the hall, etc. In one embodiment, the monitoring system 113 knows which sensors are in which apartments and the relative positions of the various apartments (e.g., which apartments are above other, adjacent to others, etc.). In one embodiment, the monitoring system 113 database includes information about sensor locations in various apartments relative to other apartments (e.g., sensor 1 in apartment 1 is on the wall opposite sensor 3 in apartment 2, etc.).

It will be evident to those skilled in the art that the invention is not limited to the details of the foregoing illustrated embodiments and that the invention can be embodied in other specific forms without departing from the spirit or essential attributes thereof, furthermore, various omissions, substitutions and changes can be made without departing from the spirit of the invention. For example, although specific embodiments are described in terms of the 900 MHz frequency band, one of ordinary skill in the art will recognize that frequency bands above and below 900 MHz can be used as well. The wireless system can be configured to operate on one or more frequency bands, such as, for example, the HF band, the VHF band, the UHF band, the Microwave band, the Millimeter wave band, etc. One of ordinary skill in the art will further recognize that techniques other than spread spectrum can also be used. The modulation is not limited to any particular modulation method, such that modulation scheme used can be, for example, frequency modulation, phase modulation, amplitude modulation, combinations thereof, etc. The foregoing description of the embodiments is, therefore, to be considered in all respects as illustrative and not restrictive, with the scope of the invention being delineated by the appended claims and their equivalents.

What is claimed is:

1. A sensor system, comprising:
   one or more sensor units, each of said one or more sensor units comprising at least one sensor configured to measure a condition, said sensor unit configured to receive instructions, said sensor unit configured to report a severity of failure value when said sensor determines that data measured by said at least one sensor fails a threshold test, said sensor unit configured to adjust said threshold from time to time according to sensor reading taken during a specified time period;
   a base unit configured to communicate with said one or more sensor units to a monitoring computer, said monitoring computer configured to send a notification to a responsible party when said severity of failure value corresponds to an emergency condition, said monitoring computer configured to log data from one or more of said sensor units when said data from one or more of said sensor units corresponds to a severity of failure value; and
   a portable monitoring unit comprising:
      a controller in communication with said one or more sensors, said controller configured to allow a user of said portable monitoring unit to remotely set a sensor threshold level of said one or more sensor units, said controller further configured to receive one or more actual sensor data threshold levels from said one or more sensor units;
      a display that displays said actual sensor data threshold levels;
      one or more input devices; and
      a transceiver configured to provide communication between a sensor system and said controller.

2. The portable monitoring unit of claim 1, wherein the sensor system sends said information upon the occurrence of a pre-defined event.

3. The portable monitoring unit of claim 1, wherein the sensor system sends said information upon request from said controller.

4. The portable monitoring unit of claim 1, wherein said measured conditions further comprises a working status of said sensors.

5. The portable monitoring unit of claim 1, wherein said controller is further configured to receive diagnostic information and display said diagnostic information on said display.

6. The portable monitoring unit of claim 1, wherein input devices comprises buttons.

7. The portable monitoring unit of claim 1, further comprising a microphone.

8. The portable monitoring unit of claim 1, further comprising an audio device.

9. The portable monitoring unit of claim 1, further comprising a sensor programming unit.

10. The portable monitoring unit of claim 1, further comprising a second transceiver.

11. The portable monitoring unit of claim 10, wherein said second transceiver is configured to communicate through cellular telephone.

12. The portable monitoring unit of claim 10, wherein said second transceiver is configured to communicate through radio transmissions.

13. The portable monitoring unit of claim 1, further comprising a location detector unit.

14. The portable monitoring unit of claim 1, further comprising a computer interface.

* * * * *